US009841811B2

(12) United States Patent
Reiner

(10) Patent No.: US 9,841,811 B2
(45) Date of Patent: Dec. 12, 2017

(54) VISUALLY DIRECTED HUMAN-COMPUTER INTERACTION FOR MEDICAL APPLICATIONS

(76) Inventor: Bruce Reiner, Berlin, MD (US)

( * ) Notice: Subject to any disclaimer, the term of this patent is extended or adjusted under 35 U.S.C. 154(b) by 458 days.

(21) Appl. No.: 12/998,554

(22) PCT Filed: Nov. 3, 2009

(86) PCT No.: PCT/US2009/005940
§ 371 (c)(1),
(2), (4) Date: Jul. 18, 2011

(87) PCT Pub. No.: WO2010/051037
PCT Pub. Date: May 6, 2010

(65) Prior Publication Data
US 2011/0270123 A1   Nov. 3, 2011

Related U.S. Application Data

(60) Provisional application No. 61/193,178, filed on Nov. 3, 2008.

(51) Int. Cl.
| | |
|---|---|
| *A61B 13/00* | (2006.01) |
| *G06F 3/01* | (2006.01) |
| *A61B 3/113* | (2006.01) |
| *A61B 6/00* | (2006.01) |
| *A61F 4/00* | (2006.01) |

(52) U.S. Cl.
CPC .............. *G06F 3/013* (2013.01); *A61B 3/113* (2013.01); *A61B 6/463* (2013.01); *A61B 6/465* (2013.01); *A61B 6/467* (2013.01); *A61B 6/469* (2013.01); *A61F 4/00* (2013.01); *A61B 6/468* (2013.01)

(58) Field of Classification Search
CPC ............ A61B 5/16; A61B 3/113; A61B 5/162
USPC ................. 600/558; 351/200, 205, 222, 246
See application file for complete search history.

(56) References Cited

U.S. PATENT DOCUMENTS

| | | |
|---|---|---|
| 6,648,820 B1 | 11/2003 | Sarel |
| 7,027,621 B1 | 4/2006 | Prokoski |
| 2005/0148894 A1 | 7/2005 | Misczynski et al. |
| 2006/0007188 A1* | 1/2006 | Reiner .......................... 345/179 |
| 2006/0190419 A1 | 8/2006 | Bunn et al. |
| 2006/0235331 A1 | 10/2006 | Kiderman |
| 2007/0066874 A1 | 3/2007 | Cook |

(Continued)

*Primary Examiner* — Daniel Cerioni
(74) *Attorney, Agent, or Firm* — Jean C. Edwards, Esq.; Edwards Neils LLC

(57) ABSTRACT

The present invention relates to a method and apparatus of utilizing an eye detection apparatus in a medical application, which includes calibrating the eye detection apparatus to a user; performing a predetermined set of visual and cognitive steps using the eye detection apparatus; determining a visual profile of a workflow of the user; creating a user-specific database to create an automated visual display protocol of the workflow; storing eye-tracking commands for individual user navigation and computer interactions; storing context-specific medical application eye-tracking commands, in a database; performing the medical application using the eye-tracking commands; and storing eye-tracking data and results of an analysis of data from performance of the medical application, in the database. The method includes performing an analysis of the database for determining best practice guidelines based on clinical outcome measures.

28 Claims, 12 Drawing Sheets

(56) References Cited

U.S. PATENT DOCUMENTS

2007/0197879 A1* 8/2007 Martz .......................... 600/300
2007/0273611 A1 11/2007 Torch
2008/0104415 A1 5/2008 Palti-Wasserman et al.
2008/0287821 A1* 11/2008 Jung .................. G06F 19/3406
                                                                   600/544
2009/0303441 A1* 12/2009 Lieberman et al. .......... 351/246

* cited by examiner

Areas of Interest

— — — Forward Tracking
— — — Backtracking

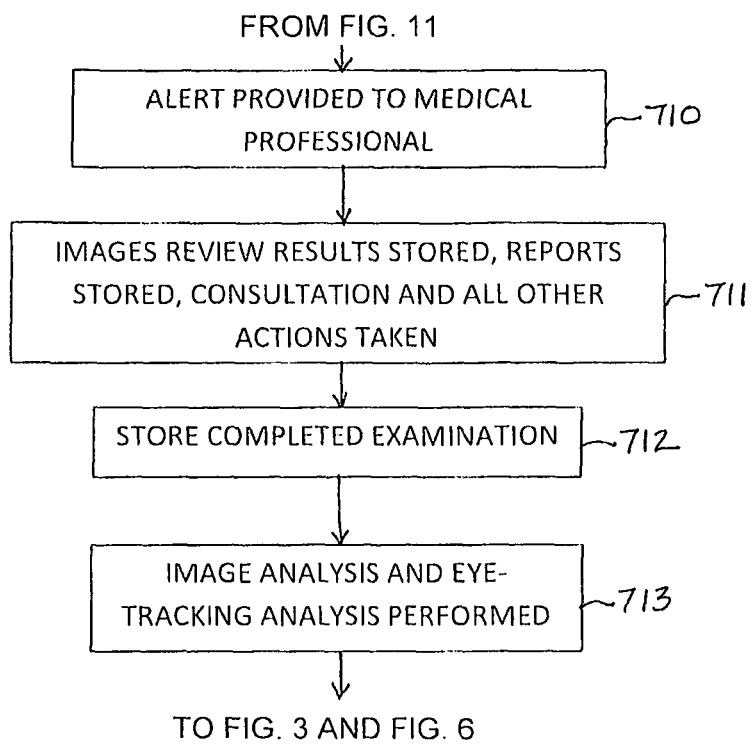

VISUALLY DIRECTED HUMAN-COMPUTER INTERACTION FOR MEDICAL APPLICATIONS

CROSS-REFERENCE TO RELATED APPLICATIONS

The present invention is a 35 U.S.C. 371 National Stage Entry of PCT/US2009/005940, filed Nov. 3, 2009, which claims priority from U.S. Provisional Patent Application No. 61/193,178, dated Nov. 3, 2008, the contents of all of which are herein incorporated by reference in their entirety.

BACKGROUND OF THE INVENTION

1. Field of the Invention

The present invention relates to alternative strategies to counteract the limitations of human-computer interaction in a medical environment, and includes eye tracking and thought recognition technologies, which provide for faster and more intuitive human-computer input.

2. Description of the Related Art

In current medical practice, human-computer interaction represents the convergence of two powerful information processors, the human brain and the electronic microprocessor; each of which has its own unique attributes and limitations. The human brain is capable of abstract thought, yet is prone to inconsistency and can be adversely affected by emotional and environmental factors. The computer brain, on the other hand, is highly consistent, indefatigable, and immune to emotional/environmental change. The problem however lies in its limited ability to process data extemporaneously, and in abstract ways. As a result, the current human-computer interaction is largely unidirectional in nature, with the human providing guidance and direction to the computer in navigating the task at hand.

In a medical practice, human-computer interaction can take a number of forms from searching and analyzing clinical data contained within the patient electronic medical record (EMR), interpretation and reporting of three-dimensional medical imaging data within the picture archival and communication system (PACS), or guidance in the performance of a technical procedure (e.g., endoscopic surgery, computerized tomography (CT) acquisition).

As computer intelligence has evolved, new computerized educational tools have been created to assist the medical practitioner with the task at hand. These computerized artificial intelligence and decision-support tools are diverse in nature and can take the form of neural networks, computer-aided diagnosis (CAD) software, and automated data mining of medical data repositories.

The primary challenge to date is to improve and facilitate the intrinsic attributes of these two divergent information processors. In the current practice environment, however, this convergence is limited by the narrow bandwidth and highly constrained interface; which typically consists of manual (in the form of an electronic mouse, keyboard, or touch screen), or verbal (speech commands) input. If the ultimate goal is to create an intuitive, rapid, and reliable bidirectional information exchange, then new strategies must be developed which address existing bandwidth deficiencies on the part of human input (speed), and improve thought and understanding between the two information processors (intuition).

SUMMARY OF THE INVENTION

The present invention relates to alternative strategies to counteract the limitations of human-computer interaction in a medical environment, and includes eye tracking and thought recognition technologies, which provide for faster and more intuitive human-computer input.

In one embodiment consistent with the present invention, a method of utilizing an eye detection apparatus in a medical application, includes calibrating the eye detection apparatus to a user; performing a predetermined set of visual and cognitive steps using the eye detection apparatus; determining a visual profile of a workflow of the user; creating a user-specific database to create an automated visual display protocol of said workflow; storing eye-tracking commands for individual user navigation and computer interactions; storing context-specific medical application eye-tracking commands, in a database; performing the medical application using said eye-tracking commands; and storing eye-tracking data and results of an analysis of data from performance of the medical application, in said database.

In another embodiment consistent with the present invention, the method includes performing a training program with the user, on the eye detection apparatus.

In yet another embodiment consistent with the present invention, the method includes making individual profiles of said eye-tracking commands available to other users for at least one of protocol optimization, education, or training.

In yet another embodiment consistent with the present invention, the automated visual display protocol results in creating an automated visual workflow templates based upon data analysis of the user and reference peer groups.

In yet another embodiment consistent with the present invention, the eye-tracking commands include at least one of blink, blink rate, gaze direction, or length of gaze.

In yet another embodiment consistent with the present invention, the method includes performing an analysis of said database for determining best practice guidelines based on clinical outcome measures.

In yet another embodiment consistent with the present invention, the method includes integrating the eye tracking apparatus with an affective computing and fatigue measuring system; and correlating eye-tracking patterns of the user with fatigue and stress measurements.

In yet another embodiment consistent with the present invention, the eye tracking apparatus becomes sensitized to changes in a user's physical and emotional state and automatically adjusts its internal sensitivity settings to said changes.

In yet another embodiment consistent with the present invention, the method includes prompting the user when changes in a user's physical and emotional state exceed a predetermined threshold.

In yet another embodiment consistent with the present invention, the method includes shutting down computer operations or mandating a rest period by the user until changes in the user's physical and emotional state return below a predetermined threshold.

In yet another embodiment consistent with the present invention, the method includes initiating a sequence of training/feedback steps due to changes in a user's physical and emotional state; and re-adjusting internal visual recognition parameters due to completion of said sequence.

In yet another embodiment consistent with the present invention, the method the eye-tracking commands include at least one of object selection, object movement, text scrolling, image scrolling, menu commands, or editing functions.

In yet another embodiment consistent with the present invention, the medical application is performed using non-command based user interactions.

In yet another embodiment consistent with the present invention, the method includes performing an analysis of eye-tracking data, including providing automated data extraction analysis on eye fixations and saccades by one of eye positioning or eye velocity.

In yet another embodiment consistent with the present invention, the medical application is a radiological application, and the method includes applying selective resolution and decompression algorithms, and specialized image processing of images obtained during the radiological application.

In yet another embodiment consistent with the present invention, the method includes modifying and refining individual user's automated visual display protocol; and processing automated visual workflow templates in accordance with the user's modified automated visual display protocol and in context with the medical application.

In yet another embodiment consistent with the present invention, the eye-tracking metrics recorded by said eye-tracking apparatus include gaze rate; gaze direction; gaze percentage; number of fixations; scan path directionality; number of instances of backtracking; frequency of long duration dwells over areas of interest; saccade length; and fixation/saccade time ratio.

In yet another embodiment consistent with the present invention, the method includes performing feedback operations with the user to assess an efficiency of the user during the medical application.

In yet another embodiment consistent with the present invention, indicators of inefficiency include backtracking over a same visual area, or fixation over a visual area.

In yet another embodiment consistent with the present invention, the method includes obtaining a baseline measure of visual acuity and fatigue of the user.

In yet another embodiment consistent with the present invention, the method includes recording visual metrics in numerical and graphical formats.

In yet another embodiment consistent with the present invention, the method includes creating visual maps, which graphically show each of said eye-tracking commands in chronological order, with timestamping of same.

In yet another embodiment consistent with the present invention, the method includes a playback function cycles through the automated visual workflow template.

In yet another embodiment consistent with the present invention, the method includes providing an alert to users when deficiencies in said eye-tracking analysis is found.

In yet another embodiment consistent with the present invention, a timing device forwards alerts to users when fixations are noted.

Finally, in yet another embodiment consistent with the present invention, an apparatus for performing a radiological application, includes an eye detection apparatus which detects eye movements of a user and creates a visual profile of a workflow of the user; an imaging device, which takes images in a medical application, of the user; and a database for recording eye-tracking information from the user and said visual profiles of the user, along with said images taken in the medical application.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

FIG. 12 is a continuation of FIG. 11.

DESCRIPTION OF THE INVENTION

Figure 1:
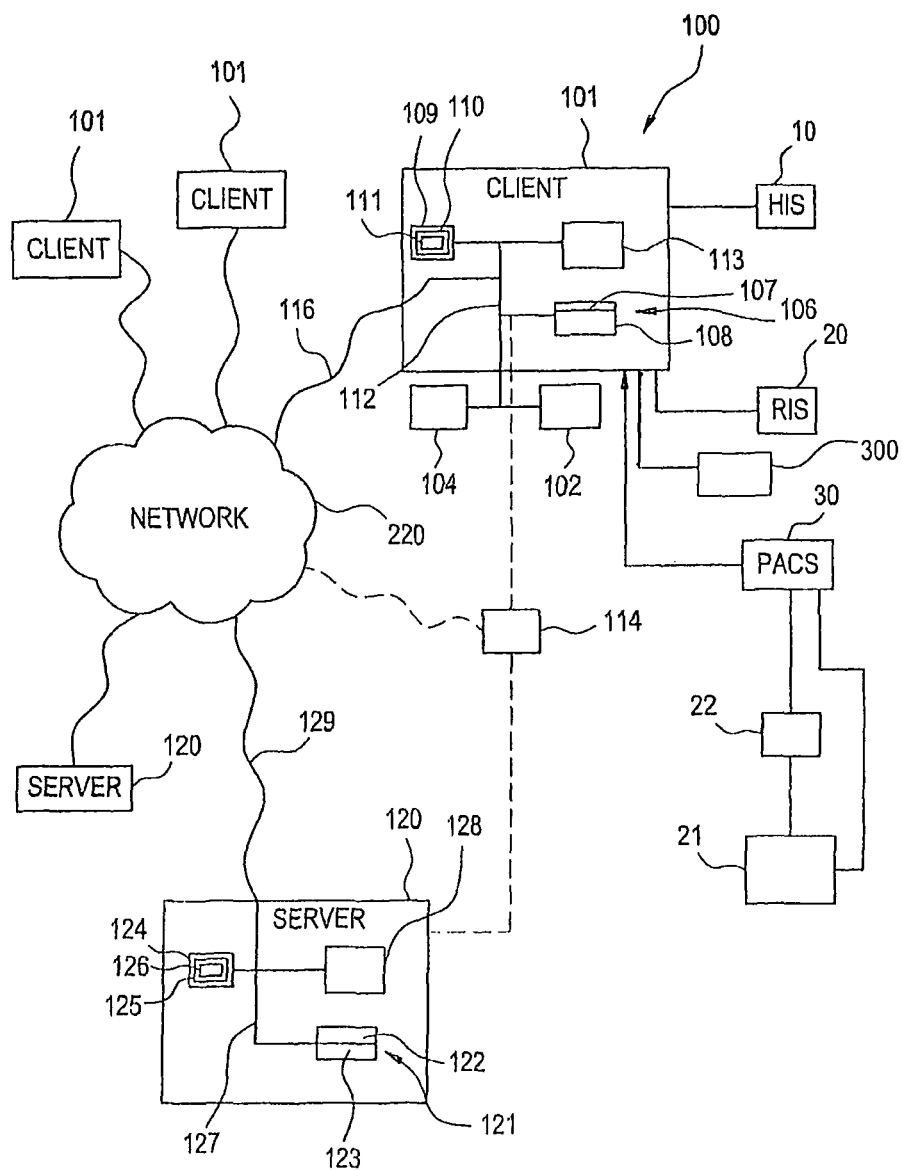
FIG. 1 is a schematic drawing of the major components of a radiological system using an eye tracker, according to one embodiment consistent with the present invention.

According to one embodiment of the invention, as illustrated in FIG. 1, medical (radiological) applications may be implemented using the system 100. The system 100 is designed to interface with existing information systems such as a Hospital Information System (HIS) 10, a Radiology Information System (RIS) 20, a radiographic device 21, and/or other information systems that may access a computed radiography (CR) cassette or direct radiography (DR) system, a CR/DR plate reader 22, a Picture Archiving and Communication System (PACS) 30, an eye movement detection apparatus 300, and/or other systems. The system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the system 100 of the present invention and the information systems, such as the HIS 10, RIS 20, radiographic device 21, CR/DR plate reader 22, PACS 30, and eye movement detection apparatus 300, etc., may be enabled to allow the system 100 to retrieve and/or provide information from/to these systems. According to one embodiment of the invention, bi-directional communication between the system 100 of the present invention and the information systems allows the system 100 to update information that is stored on the information systems. According to one embodiment of the invention, bi-directional communication between the system 100 of the present invention and the information systems allows the system 100 to generate desired reports and/or other information.

The system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely. According to another embodiment of the invention, the client computers 101 may include several components, including processors, RAM, a USB interface, a telephone interface, microphones, speakers, a computer mouse, a wide area network interface, local area network interfaces, hard disk drives, wireless communication interfaces, DVD/CD readers/burners, a keyboard, and/or other components. According to yet another embodiment of the invention, client computers 101 may include, or be modified to include, software that may operate to provide data gathering and data exchange functionality.

According to one embodiment of the invention, an input device 104 or other selection device, may be provided to select hot clickable icons, selection buttons, and/or other selectors that may be displayed in a user interface using a menu, a dialog box, a roll-down window, or other user interface. In addition or substitution thereof, the input device may also be an eye movement detection apparatus 300, which detects eye movement and translates those movements into commands.

The user interface may be displayed on the client computer 101. According to one embodiment of the invention, users may input commands to a user interface through a programmable stylus, keyboard, mouse, speech processing device, laser pointer, touch screen, or other input device 104, as well as an eye movement detection apparatus 300.

According to one embodiment of the invention, the client computer system 101 may include an input or other selection device 104, 300 which may be implemented by a dedicated piece of hardware or its functions may be executed by code instructions that are executed on the client processor 106. For example, the input or other selection device 104, 300 may be implemented using the imaging display device 102 to display the selection window with an input device 104, 300 for entering a selection.

According to another embodiment of the invention, symbols and/or icons may be entered and/or selected using an input device 104 such as a multi-functional programmable stylus 104. The multi-functional programmable stylus may be used to draw symbols onto the image and may be used to accomplish other tasks that are intrinsic to the image display, navigation, interpretation, and reporting processes, as described in U.S. patent application Ser. No. 11/512,199 filed on Aug. 30, 2006, the entire contents of which are hereby incorporated by reference. The multi-functional programmable stylus may provide superior functionality compared to traditional computer keyboard or mouse input devices. According to one embodiment of the invention, the multi-functional programmable stylus also may provide superior functionality within the PACS 30 and Electronic Medical Report (EMR).

In one embodiment consistent with the present invention, the eye movement detection apparatus 300 that is used as an input device 104, may be similar to the Eye-Tracker SU4000 (made by Applied Science Laboratories, Bedford, Mass.) with head-tracking capability. In one embodiment, the user is fitted with a headband 301 upon which the optical recording system 302 is mounted. The optical recording system 302 includes a sensing device 303, such as an infrared (IR) light-emitting diode and phototransistor detectors (optics module), which is mounted on the headband 301. The IR light is emitted and reflects off an IR reflective visor 304 into the left eye 305. The IR light then reflects back off the pupil and cornea of the eye 305 to the visor 306, which then reflects it back to a charge-coupled device camera 307 located next to the optics module 303. The system 302 computes line of gaze and dwell time based on pupil and corneal reflection parameters. However, other types of eye tracking devices may be used, as long they are able to compute line of gaze and dwell time with sufficient accuracy.

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, 300, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101.

According to one embodiment of the invention, the client computer 101 may include an image display device 102 which may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the system 100 may include separate programs 110 having code that performs desired operations. According to one embodiment of the invention, the program 110 that runs the system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, the system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines. According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, the PACS 30 (if separate), and the eye movement detection apparatus 30, are shown as directly coupled to the client computer 101, it is known that these systems may be indirectly coupled to the client over a LAN, WAN, the Internet, and/or other network via communication links. Further, even though the eye movement detection apparatus 300 is shown as being accessed via a LAN, WAN, or the Internet or other network via wireless communication links, it is known that the eye movement detection apparatus 300 could be directly coupled using wires, to the PACS 30, RIS 20, radiographic device 21, or HIS 10, etc.

According to one embodiment of the invention, users may access the various information sources through secure and/or non-secure interne connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition or eye movement detection. According to one embodiment, user interfaces may be provided that support several interfaces including display screens, voice recognition systems, speakers, microphones, input buttons, eye movement detection apparatuses, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system or eye movement detection apparatus 300 to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment.

Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems of the present invention may contain additional or different components.

The present invention utilizes the detection of eye movements (i.e., eye tracking) in order to provide a reliable mechanism for more direct, and faster human-computer input. On the other hand, thought recognition provides a means to enhance intuition, particularly when combined with pre-existing user and context-specific behavior (which can be stored, accessed, and analyzed through database mining).

In particular, eye tracking has been used as an alternative input strategy and found to be especially useful in those individual users who have lost voluntary motor control due to illness or injury, yet retain the ability to control eye movements. A small body of research has been performed which has investigated the comparative speed of eye movements to conventional manual input (e.g., electronic mouse), and results show that simple target selection and cursor positioning operations could be performed approximately twice as fast with an eye tracker as a comparable mouse.

An additional (and overlooked) benefit of eye tracking input is that it eliminates the "wasted" visual effort associated with manual input devices (e.g., mouse, keyboard), in which the end-user looks at the destination he/she wishes to move before doing so. By doing so, the eye movement serves as an indicator of the user's goal before actually using the input device 104. These repetitive eye movements have the net effect of distracting the end-user from their task, increasing the task completion time, and introducing visual fatigue. Eye tracking as an alternative input provides the theoretical advantage of eliminating these repetitive "wasted" movements, by replacing manual input with visual input.

One area where eye tracking has been effectively used in the human-computer interaction is in flight simulation, where manual input by the operator is restricted by equipment operation. In this scenario, eye movements have been used to create the illusion of a larger and higher resolution image than can actually be rendered. Using this approach, the portion of the display on the equipment console that is being viewed is depicted in high resolution, while the surrounding area (visible only in peripheral vision) is depicted in lower resolution.

Figure 2:
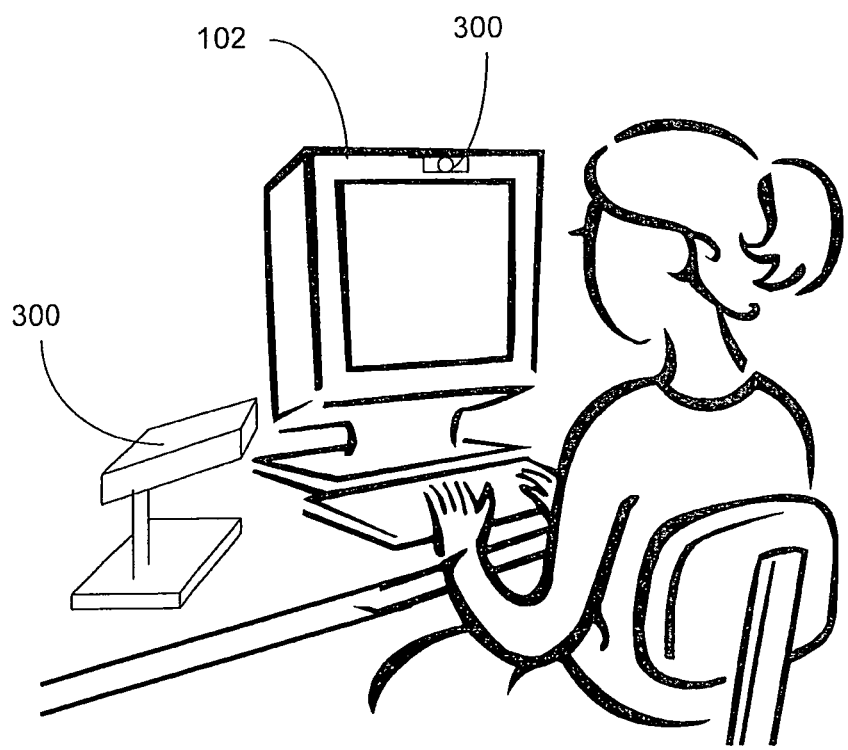
FIG. 2 is diagram of an apparatus showing an eye tracker and a display, according to one embodiment consistent with the present invention.

Eye movements are recorded with highly specialized equipment (see FIG. 2), which can be integrated into the display 102, or can be provided in a separate device 300. Typically, eye movement detection devices 300 record two major parameters of visual search. The first is generally referred to as visual dwell, and reflects the amount of time the observer spends looking at or fixating on a given location in a scene with foveal or high-resolution vision. The second parameter measures how the eye moves from one location to the next (i.e., between fixation points), both in terms of direction and speed. These jumps between fixations are referred to as "saccades". These are voluntary relocations of fixations around a scene used to acquire visual information. They typically have a latency of 100 to 150 milliseconds and velocity of 30° to 100° of visual angle per second. There is evidence that saccade latencies and velocities may slow with aging.

Eye position is recorded using an eye movement detection apparatus 300 such as the Eye-Tracker SU4000 (made by Applied Science Laboratories, Bedford, Mass.) with head-tracking capability. Observers are typically seated about 60 cm from the display monitor 102 for an initial calibration, during which they are not allowed to change their viewing angle, distance from the monitor 102, or head position. After calibration and during use, the user is free to move forward or side-to-side as their head movements are tracked with a magnetic head tracker 308 that automatically integrates the head-position data with the eye-position data. However, in other embodiments, the eye tracking apparatus 300 is included in the monitor 102 (see FIG. 2).

The accuracy of the eye movement detection apparatus 300 (spatial error between true eye position and computed measurements) should be less than 1°. The eye movement detection apparatus 300 samples eye positions every 1/60 of a second to generate raw x-, y-coordinate eye-position data. Fixations are then formed by the program 110 of the client computer 100 (or server 200) by grouping x and y coordinates of the raw data using a running mean distance calculation having a 0.5° radius threshold. Dwell time can be calculated by the program 110 for each fixation summated and is represented as the areas of circles in scan-path graphics. Focal attention or the so-called useful visual field is assumed to extend to pictorial or image features as far away as 2.5° from the center of a fixation. Peripheral vision extends beyond the useful visual field to encompass the entire visual field and also processes useful visual information, but not at the high level of resolution that foveal vision can process details.

Using the concept of the useful visual field, the program 110 correlates the fixation data with image locations. If a fixation is within a radius of 2.5° of a marked location, it is determined a "hit" by the program 110. If multiple fixations are associated with a given location (i.e., the observer looked at a location, looked somewhere else, and then returned to that location), the fixations were grouped into fixation clusters and their dwell times cumulated by the program 110.

Scan-paths in eye-position studies represent saccadic eye movements. Saccades are part of the saccadic eye movement system and have been extensively studied by neurophysiologists. The physiologic function of saccades is to move the eyes around a scene, locating interesting details and building up a mental "map" representing the scene. Humans benefit from saccadic eye movements as only the central part of the retina has a high concentration of color photoreceptor cells. The rest of the retina is made up of monochrome photoreceptor cells, which are well suited for motion detection but not fine vision. The eyes move so that small parts of the scene can be centered in the foveal where visual acuity is the greatest. In the present invention, special attention is paid to eye movements, based on the hypothesis that eye movements may reflect meaningful differences in the cognitive abilities of novice and expert pathologists.

Figure 3:
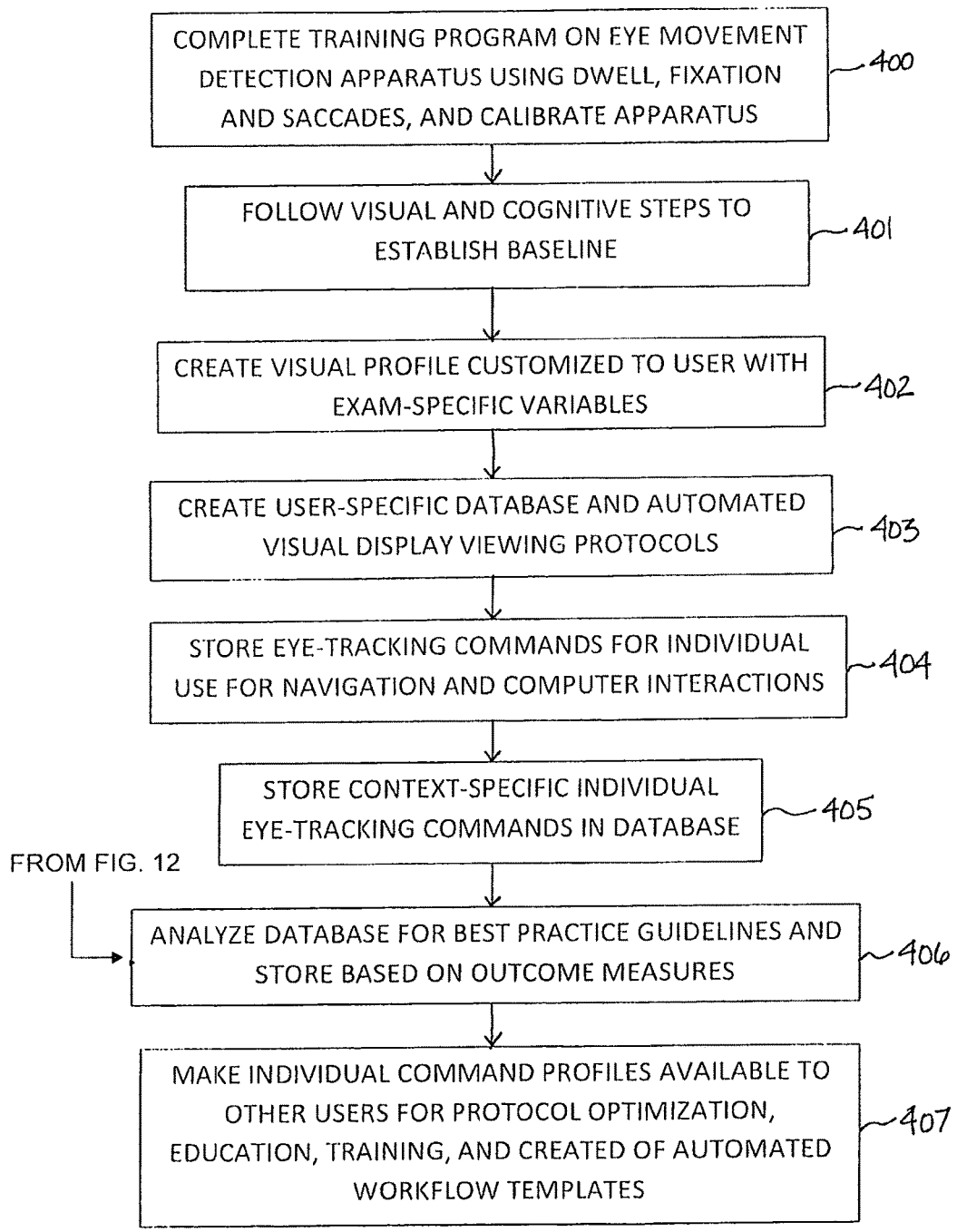
FIG. 3 is a flowchart showing the major steps in using an eye-tracking apparatus in a medical application, according to one embodiment consistent with the present invention.

A computerized training module of the program 110 trains the user in how to use the eye tracking apparatus 300 for medical applications, and provides the user feedback options to better calibrate the apparatus 300 (see FIG. 3, step 400). In particular, the user is presented by the program 110 with a series of questions regarding individual preferences for data presentation (i.e., as to how the eye tracking feedback is analyzed and presented to the user, as well as how recommendations for more efficient use are presented). As an example, one user may request that recommendations for improved eye tracking be presented on a bi-weekly basis with correlative eye tracking data from all peers. Another end-user may request that eye tracking recommendations be presented whenever a potential workflow modification in excess of 5% is identified, and may only use the reference data of a specific sub-group of end-users (e.g., sub-specialist radiologists within academic practice). The training program 110 may include a series of modules designed to facilitate improved eye tracking efficiency and to identify specific instances of inefficiency. Using this data, the training program 110 can in turn be used to create user-specific automated eye tracking workflow templates, which combine each individual user's style with those of similar, more efficient end-users.

The present invention can be used in any type of application, but the exemplary embodiment is for any type of medical specialist and type of medical applications, which will be described in detail below. In particular, those applications which are centered around imaging data (e.g., radiology, ophthalmology, pathology) are best suited for this application, since the data is inherently visual in nature and therefore, driven by image perception and eye tracking.

In an imaging medical application consistent with the present invention, within the normal course of image review and interpretation, a clinician or radiologist will typically follow a pre-defined set of visual and cognitive steps (see step 401), which tend to be pre-determined based upon the anatomy (e.g., chest), modality (e.g., radiography), clinical indication (e.g. trauma), and experience/training of the individual end-user (e.g. radiologist).

Figure 4:
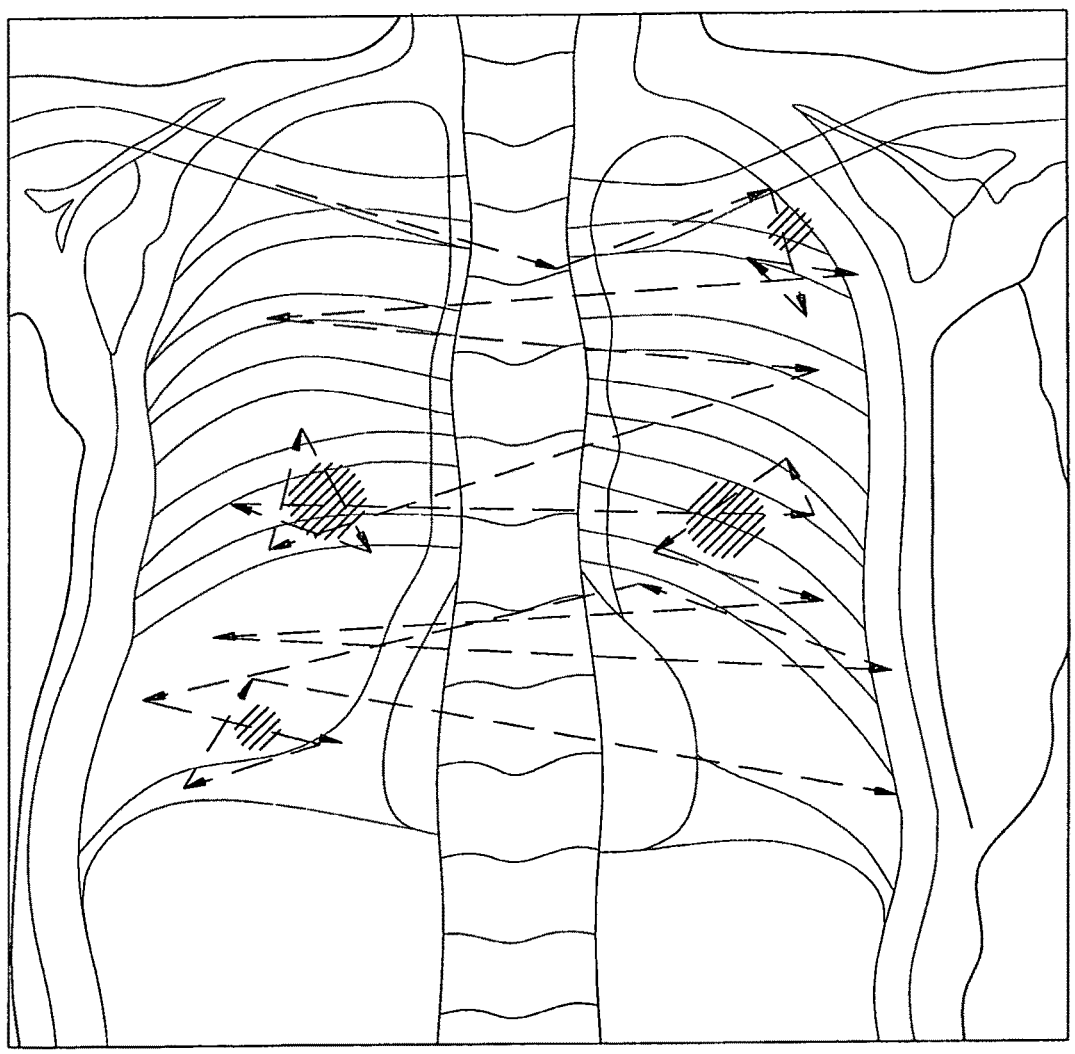
FIG. 4 is a diagram of a chest X-ray showing fixation points and directionality of gaze, in an eye-tracking medical application, according to one embodiment consistent with the present invention.

A few examples of eye tracking patterns which a radiologist may undergo when reviewing a chest radiographic examination include the following (see FIG. 4, for example):

1) Geographic sweep beginning at the upper left hand corner of the image and moving across and downward (left to right, up to down) in a sequential order.

2) Bisection of the image into two (or more) components, with sequential visual scanning of each individual component in horizontal and vertical directions.

3) Segmentation of the imaging dataset into individual anatomic regions (e.g., ribs, lung fields, heart/blood vessels), with sequential review of each individual component, followed by a comprehensive sweep of the entire image.

It is important to recognize that these "steps" are both common across observers but also unique to each observer. For example, one reader may start in the upper left corner of an image and scan clockwise, while another may start in the lower right and circle counter-clockwise. At the global level, they both engage in a relatively circular scan of the image, but at the individual level their exact strategies are unique to the individual. Thus, there are both commonalities between the patterns as well as differences.

Once the individual end-user's visual profile is determined by the program 110 in FIG. 3, step 402, the sequential workflow steps can be predicted in a reliable fashion and recreated each time that individual reviews that specific type of imaging dataset. In this manner, a user-specific visual profile can be created by the program 110 which takes into account the individual user's eye tracking preferences, along with exam-specific variables such as the anatomy, modality, and clinical indication.

Thus, an individual end-user's eye tracking tendencies is often dependent upon the specific task at hand, the type of data being presented, as well as the specific format of the data presentation. An end-user tasked with formal interpretation of both a mammogram and breast MRI (same anatomic region, but different types of data and presentation states), would use different eye tracking patterns for the two different data sets. At the same time, if the display presentation was altered (e.g., MRI data displayed using 4 on 1 format instead of 1 on 1 display format), the corresponding eye tracking patterns may also change. As for the task at hand, if a radiologist was reviewing a mammogram, as opposed to rendering a formal interpretation, his/her eye tracking pattern may be different, since the requirements for formal interpretation are more rigorous than those for a simple review. One can see that multiple variables would come into play when characterizing each user and context-specific eye tracking profile.

This leads to the creation of a user-specific database 114 which can be accessed by the user, using biometrics, for example, which leads to the creation of automated visual display viewing protocols in step 403. An automated display viewing protocol is a visual alternative to an automated workflow template, which effectively creates "hands free" navigation. In both cases, the end-user effectively lets the computer drive through the creation of an automated workflow template, which has been created based upon data analysis of the individual end-user, reference peer groups, and the many individual variables described. The automated visual display viewing protocol would effectively create a movie in which the end-user's eyes could remain fixed on a central point and the data would effectively move to recreate the normal sequence of eye movements performed on a stationary imaging set.

In addition to the manner in which the imaging data is sequentially reviewed (i.e., eye tracking protocol), the program 110 will also store in the user-specific imaging database 114, the specific eye tracking commands each individual uses for navigation and other computer interactions in step 404. Types of Visual Input Commands include: 1) Blink; 2) Blink rate; 3) Gaze direction; 4) Length of gaze; and 5) Combinations of the above.

As an example, one user may use directed eye movements followed by an extended gaze to direct activation of certain workstation tools. In this manner, the end-user would direct their gaze to a magnification icon on the tool bar, which in turn would instruct the program 110 to activate the magnification tool. The end-user would cancel the magnification tool by double blinking, for example, which in effect prompts the program 110 to cancel or deactivate the preselected tool.

Another user may instead prefer to activate the magnification function by a different eye tracking command (e.g., upward gaze) or a slight head tilt to the right. The specific user-specific preferences of each command-based interaction would be stored in that specific user's database 114 by the program 110, so that the program 110 would recognize and translate each end-user's commands into the specific computer-based interaction being requested. In a manner similar to speech recognition software, the eye tracking software program 110 would be "trained" by the end-user to recognize individual eye tracking commands. The speed and magnitude of one end-user's command (e.g., upward gaze) may be slightly different from the same command of another end-user. These subtle variations in each individual end-user would be stored in the database 114, tracked, and analyzed by the program 110, so as to improve recognition accuracy in an iterative fashion.

These command-based interactions would be both user and context specific, as in step 405, so that exam-specific variables may vary for an individual end-user in accordance with the specific task at hand. As an example, a radiologist interpreting a chest CT and chest radiograph (x-ray) may have different command-based interactions for the two different studies. A commonly-used computer software tool used in the interpretation of a chest radiographic image is contrast adjustment (window/level), which can be activated by clockwise or counter-clockwise rotation of gaze, for example. Instead of subtle contrast adjustment for CT interpretation, the radiologist instead will direct the program 110 to switch from one window/level setting (e.g., lung fields) to another window/level setting (e.g., soft tissue), by using the same clockwise/counter-clockwise visual command. In this manner, the visual command for the same end-user varies in accordance with the specific exam type or anatomic region being evaluated.

Each of these user and context-specific eye tracking commands are stored in a master database 114 by the program 110 in step 405, so that it becomes portable and accessible to the individual end-user wherever he/she is working. At the same time, data mining can be performed by the program 110 to analyze, and identify "best practice" guidelines in step 406, which are stored in the database 114, based on a number of outcome measures (e.g., diagnostic accuracy, interpretation time, end-user fatigue). The end-users with the highest outcome measures can have the program 110 make their individual command profiles available to other users for the purposes of protocol optimization, education and training, and creation of automated workflow templates, by the program 110 in step 407.

Figure 5:
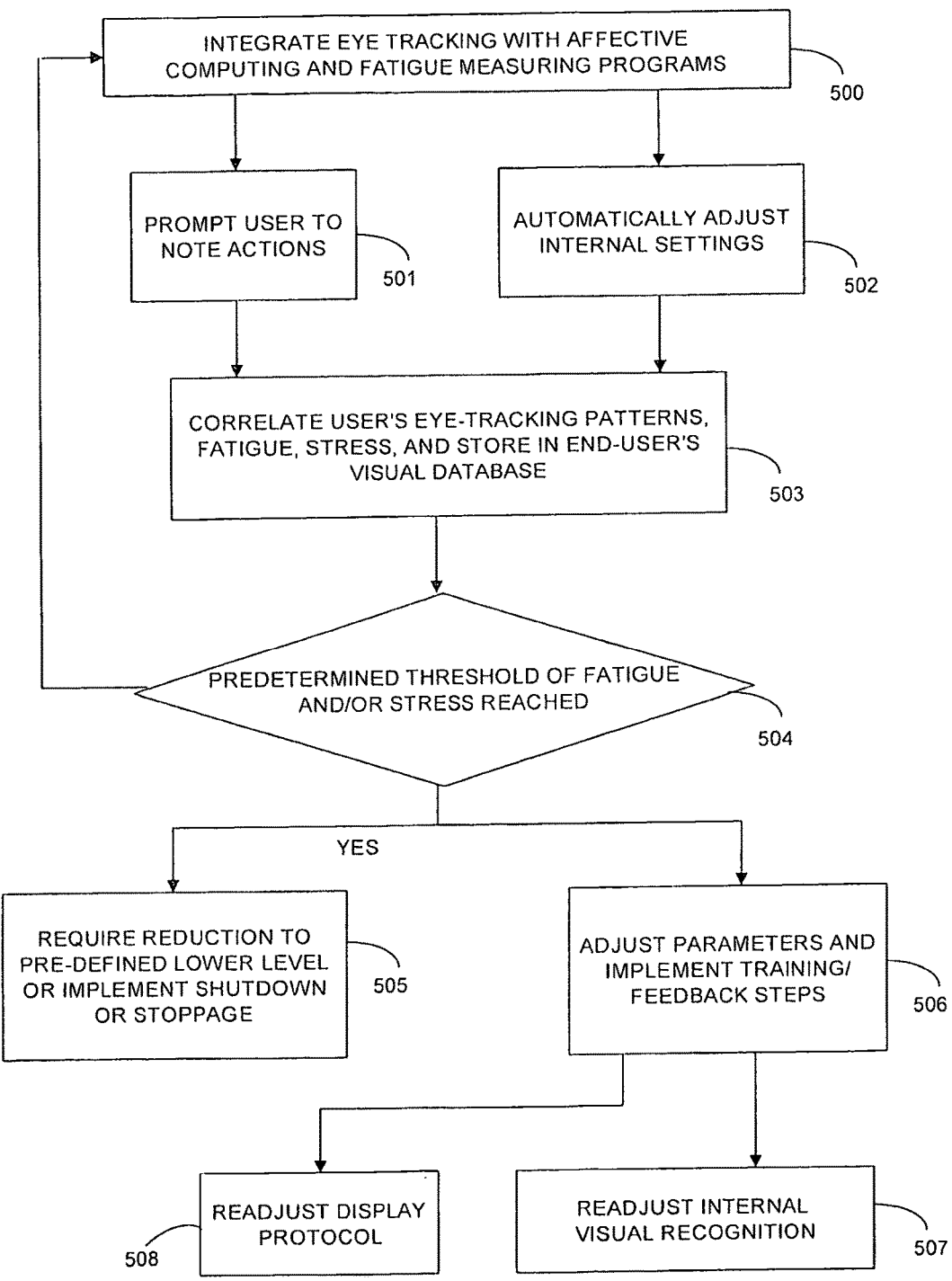
FIG. 5 is a flowchart showing the major steps in integrating eye-tracking with fatigue and/or stress measurements in a medical application, according to one embodiment consistent with the present invention.

One of the technical challenges associated with alternative navigation through eye tracking is the reality that an individual end-user's eye tracking acuity may change over time, as stress and fatigue levels vary. The same iterative "learning" response which occurs over time as an individual end-user and the computer program 110 become familiar with one another, can also occur and effect changes. The individual user becomes experienced with the program's 110 eye tracking recognition capabilities, while the program 110 becomes familiar with intra-user variability in eye tracking commands. At the same time, the eye tracking software program 110 can be instructed to become integrated with affective computing and fatigue measuring software programs 110 (see FIG. 5, step 500), so that as stress and fatigue levels change over time, the eye tracking program 110 becomes sensitized to the user's changing emotional state and makes automatic accommodations in accordance to these changing levels, to keep a minimal baseline of efficacy.

For example, as an individual end-user's fatigue levels increase, eye lids can begin to sag, and the eye tracking program 110 may prompt the end-user so that they can become aware of their actions, or the program 110 can adjust its own internal sensitivity settings automatically to the changes. Specifically, if the end-user fatigue reaches a pre-defined critical threshold, the program 110 may provide a feedback signal to the end-user (e.g., high frequency audible cue or flashing light) which alerts them as to the impending problem, in step 501. Another response by the program 110 could be adjustment of the eye tracking software sensitivity settings required to initiate program 110 actions, in step 502. The correlation between each individual end-user's fatigue, stress, and eye tracking patterns may be included as an integral part of the user's visual database 114 in step 503. This allows for the "auto-regulation" by the eye tracking software program 110 as fatigue and stress levels change over time.

Another option may include the program 110 actually shutting down computer operations until measured fatigue levels return to a pre-defined acceptable threshold level. Therefore, if a pre-determined threshold of fatigue and/or stress is measured by the eye tracking apparatus 300 in step 504, the program 110 may require a reduction to a pre-defined lower level, or stoppage, before proceeding with the required task, in step 505. In one example, if an airline pilot has high levels of fatigue, the program 110 may require him/her to rest before allowing them to proceed for safety and operational efficiency measures.

In addition to modifying the eye tracking recognition sensitivity settings, the computer program 110 can adjust other parameters, in step 506, in accordance with eye tracking performance measures. If, for example, an individual user's eye tracking commands begin to demonstrate reduced recognition based upon the program's 110 analysis, a brief training program can be initiated by the program 110, which calls for the user to follow a sequence of training/feedback steps which the computer program 110 can use to readjust its own internal visual recognition software in step 507, after completion of the task at hand, thereby not adversely affecting workflow.

The computer program 110 could also modify its own display protocol to maximize eye tracking performance, in step 508. This could take the form of monitor 102 brightness adjustment, switch from monochrome to color display, alteration in monitor 102 resolution, or changes in the user interface (UI), which may be particularly important if navigation is done through eye fixation on toolbar icons. The net result is that the interaction between user eye tracking and computer recognition is a dynamic process, where the program 110 continuously adjusts and responds to changes in user affect, eye tracking recognition, and the specific task at hand.

The aforementioned description of how the human/computer interaction takes place has centered on command-based eye tracking interactions, which can take a number of forms.

1) Object selection (activation of a specific computer function (e.g., magnification tool) by visually selecting an icon from the computer tool bar (i.e., activation of a specific computer function (e.g., magnification tool)).

2) Moving an object (physically relocating a visual object from one point in space to another (e.g., repositioning a current image alongside a prior image for side by side comparison), using a command-based eye tracking interaction, for example.

3) Scrolling text or imagery (activation of a cine function which allows the user to view continuous text, numerical, or imaging data files (e.g., review of a prior CT text report, review of patient's sequential laboratory values, sequential display of synchronous CT images from a multi-image dataset). Thus, the program 110 may also scroll text or imagery using command-based eye tracking interactions (activation of a cine function which allows the user to view continuous text, numerical, or imaging data files (e.g., review of a prior CT text report, review of patient's sequential laboratory values, sequential display of synchronous CT images from a multi-image dataset).

4) Menu commands (selection of individual option from a pull-down menu).

5) Editing function (medication of an existing report or individual finding).

6) Application selection (activation of a computer-based application (e.g., CAD).

The program 110 may also allow selection of menu commands (selection of individual option from a pull-down menu) using command-based eye tracking interactions, or editing functions (medication of an existing report or individual finding), or selection of applications (i.e., activation of a computer-based application (e.g. CAD)), among other commands or applications known to one of ordinary skill in the art. Commands would include, for example:

1) Creation of eye tracking navigation commands.

2) Customization of eye tracking/thought recognition command profile to individual user.

3) Customization of tracking command profile to context-specificity.

4) Storage of user-specific and context-specific eye tracking commands into master database.

5) Access of these commands tied to biometrics.

6) Integration of eye tracking command profile into user and context-specific automated workflow templates.

8) Creation of new eye tracking navigational commands from "best practice" workflow (PWI) database 113, 114.

9) Integration of alternative eye tracking software functions (e.g., fatigue, accommodation) and affective computing (e.g., stress) to provide feedback as to operational efficiency.

10) Automated adjustment of visual display data (e.g., UI, monitor brightness, resolution, color) in accordance to changes in eye tracking feedback measures.

11) Ability to edit automated workflow templates through eye tracking commands (e.g., skip, delete, add).

12) Integration of reporting functionality through eye tracking (e.g., fixate on image finding and/or symbol (i.e., in Gesture-based reporting (GBR)) and "add to report" through eye tracking command (e.g., fixate and drag to report). In addition, report findings can be edited in a similar manner to the GBR Editing Tool of U.S. Pat. No. 7,607,079 (the contents of which are herein incorporated by reference in its entirety), using eye tracking commands as the input to editing (e.g., increase, decrease, resolution, new, etc.).

13) Integration of other computerized functions (e.g., decision support) through eye tracking.

14) Ability to perform database mining and data extraction through eye tracking commands.

15) Ability to edit decision support output through eye tracking commands (e.g., add, delete, or re-prioritize differential diagnosis), (accept or reject CAD findings).

16) Ability to adjust visual display protocols through eye tracking commands (e.g., change image display format, change cine speed, change imaging plane, readjust hanging protocol).

17) Visual directed feedback.

In these command-based interactions, the end-user issues a specific command to the computer 101 (i.e., prolonged gaze on a fixed point) and the computer program 110 will respond in a pre-defined manner (e.g., magnification). Using command-based eye tracking interactions, there is a formal receipt and response by the program 110 to explicit commands issued by user input (e.g., blink, eye rotational movement).

An alternative manner in which eye tracking can be used for navigation is through non-command based interaction. In non-command based user-computer interactions the computer program 110 passively monitors the end-user using the eye tracking system 300 and responds appropriately (based on a pre-defined algorithm) based on its analysis of the end-user's eye movements. These non-command based interactions can be programmed to be both context and user-specific, so that the pre-defined interactions are inextricably tied by the program 110 to the task being performed (i.e., context specificity) and the individual profile of the end-user (i.e., user specificity). These context and user-specific algorithms can be integrated into the previously described applications of U.S. Pat. No. 7,593,549, and U.S. patent application Ser. No. 11/586,580, filed May 10, 2007, the contents of both of which are herein incorporated by reference in their entirety, as described in the following example.

In this example of non-command based interactions through eye tracking, the end-user is a radiologist tasked with the interpretation of a CT scan in the diagnosis of pulmonary embolism (i.e., blood clot in the lungs). The identification/authentication of the end-user is achieved through biometrics, where the program 110 thereafter triggers a query of the individual end-user's customized profile from the RIS/PACS/EMR databases, for the specific task at hand. The user-specific profile is in turn cross-referenced by the program 110 with the user-profile databases 113, 114 (see U.S. patent application Ser. No. 11/586,580) to provide automated workflow templates to the user, which have been designed in accordance with the individual end-user's profile (i.e., specific to Dr. Jones), anatomic region being studied (i.e., thorax), imaging data acquired (i.e., CT angiography), and clinical indication (i.e., suspected pulmonary embolism). Based on these user and context-specific inputs, the appropriate automated workflow template is identified by the program 110 and is initiated with a visual command by the user (e.g., eye blink). As the program 110 begins running the automated workflow template through a sequence of events (e.g., image display, navigation, and processing); the radiologist workflow becomes directed through a series of non-command based interactions between the end-user (radiologist) and the client computer 101.

Note that the automated visual display templates have built in editing functionality, in a manner similar to a visual remote. The end-user can slow down, speed up, skip, fast forward, or rewind through a series of visual eye commands.

As an example, during the process of image display and navigation, the program 110 running the automated workflow template calls for sequential navigation of the imaging dataset using a 4 on 1 image display format for the left-hand computer monitor 102 (in a two-computer monitor configuration). In this type of format the computer screen 102 will be segmented into 4 quadrants, with each quadrant displaying a different type of imaging data. The upper left quadrant mat displays the imaging dataset in a 2-D axial plane, the upper right quadrant displays the same imaging dataset in a 2-D coronal plane, the lower left quadrant displays the imaging dataset using a 3-D reconstruction algorithm, and the lower right quadrant displays the imaging dataset with a computer aided detection (CAD) overlay.

Based on the specific user profile for this radiologist (i.e., Dr. Jones), the "active" dataset is simultaneously displayed by the program 110 on the right hand computer monitor 102 using a 1 on 1 display format (a single image filling the entire computer screen). As Dr. Jones navigates through the "active" dataset on the right computer screen using a pre-defined cine speed, he can effectively speed up or slow down the cine rate through passive eye commands. In this scenario, the eye tracking program 110 detects the speed with which Dr. Jones' eyes circumvent the imaging data on the "active" image, and adjusts this speed accordingly.

In another example of how non-command based interactions can take place, is the situation where one image format display is activated by the program 110 and the order in which activation occurs is determined by the program 110. As an example, the user and context specific profiles for this particular case call for the order of display activation by the program 110 to be:

1) Upper left (2-D axial); 2) Upper right (2-D coronal); 3) Lower left (3-D); and 4) Lower right (CAD overlay).

If this automated workflow template by the program 110 is followed, the second set of images (2-D coronal) would be displayed by the program 110 immediately following completion of the first set of images (2-D axial). The completion of the first set would be recognized by the program 110 by the completion of sequential image review and localization of Dr. Jones' eye movements on the last image's endpoint (lower right hand corner of the image).

The second (pre-defined) set of images would then be activated by the program 110 on the right hand screen and Dr. Jones would begin navigating through these sequential images, beginning with the first image from that particular dataset.

In this specific example, however, Dr. Jones electively chooses to review comparable data points in orthogonal planes from the "middle" of the individual sequences. For example, if Dr. Jones identifies (as registered by the program 110 through eye tracking software and gaze fixation) a focal point in the axial imaging plane suspicious for a small embolism (i.e., blood clot), rather than continue to navigate through the remainder of the 2-D axial dataset, Dr. Jones instead wishes to deviate from the automated (pre-defined) workflow template and instead view the anatomic region of interest (e.g., second order right lower lobe pulmonary artery) in the orthogonal (e.g., 2-D coronal) plane. By simply redirecting his visual path to the corresponding screen (lower left hand quadrant, left hand computer monitor), Dr. Jones passively shifts from the axial to the coronal imaging plane on the right hand monitor. Rather than starting from image 1 of the full dataset, the program 110 automatically orients the sequence of imaging data to display the comparable anatomic region of interest which corresponds to the previously visualized abnormality (e.g., image 42 out of 120).

Rather than continue through the entire imaging dataset in the coronal plane, Dr. Jones elects to return to the axial imaging plane on the last image reviewed (e.g., image 142 out of 350). By returning his gaze to the upper left hand quadrant of the left hand monitor, this action is automatically performed by the program 110, with the 2-D axial imaging set now "active" on the right hand monitor 102 by the program 110, which then returns to, and displays, the last image reviewed.

After completing review of the axial dataset (for pulmonary embolism detection), Dr. Jones elects to review the axial imaging data using a different set of image processing parameters (for lung nodule detection) using command-based eye tracking interactions. This can be done by shifting his visual attention to the tool bar and actively selecting (through eye tracking), the lung nodule detection icon.

This sequence of events illustrates how the end-user can combine visual command and non-command based interactions to complete the desired task, even for something as complex as CT interpretation. The same technology can be used by other professionals, such as a CT technologist, whose job includes image acquisition, processing, and quality assurance.

In the example of a CT technologist, for the performance of a CT exam acquisition, the technologist also begins with identification/authentication using biometrics. Whereas the radiologist job takes place at the PACS 30 workstation (with embedded or external Biometrics), the technologist works instead at a CT console (which also had Biometrics integration). When the technologist signs into the CT system 40, his/her identification are cross-referenced by the program 110 with their credentials to ensure they have the appropriate training and authentication to perform the exam requested (CT angiography). If any questions or clarification is required, the program 110 will prompt the technologist to answer any questions, which can be performed through the eye tracking program 110.

In this particular example, the exam (CT angiography) calls for administration of intravenous contrast through a power injector. When the technologist (i.e., Ms. Smith) signs into the system, the RIS database 20 is queried by the program 110, and the program 110 locates information in the database 113, 114 that the technologist has not been trained (and credentialed) for use of the new power injector. In order to proceed, the technologist must either complete training, or have a credentialed user sign into the system and accept responsibility for the injection portion of the exam. By answering a series of screen prompts from the program 110, through eye navigation, the CT technologist enlists the services of a colleague (i.e., Mr. Doe) who, has successfully completed training on the new power injector. The program 110 queries the technologists to determine which technologist's workflow template will be used for image processing, and provides same to the user.

Once the injection has been completed and Mr. Doe signs off (using visual inputs to signal task completion), the program 110, using the RIS 20, allows Ms. Smith to perform the remaining tasks of image acquisition, processing, and quality assurance. Once again, the program 110 provides the option for automated context and user-specific workflow templates.

In one example, during the process of image acquisition, the technologist notices that a portion of the upper lung fields were not visualized in their entirety and directs the program 110 to perform an additional sequence of the desired area through visual commands (e.g., eye fixation on an "additional sequence" option, followed by eye tracking over the upper lung fields on the 3-dimensional anatomic reference map), which results are stored by the program 110, along with the other data.

Before signing off on the case, the technologist reviews the acquired dataset and clinical support data presented by the program 110, for completeness and overall quality. This quality assurance task can be integrated with an automated quality assurance program (see U.S. patent application Ser. No. 11/412,884, filed Apr. 28, 2006, the contents of which are herein incorporated by reference in their entirety), by the program 110 for automation and objective assessment. In using this program 110, computer program 110 algorithms would analyze the comprehensive dataset for different quality indicators (e.g., motion, artifacts, positioning) and provide an objective set of data for review by the technologist before accepting or rejecting the acquired dataset for final interpretation.

As an additional feature of the automated quality assurance program, the program 110 would include clinical (as opposed to image) data in the comprehensive assessment of exam quality. If in this example, the requisite clinical data was incomplete, the program 110 may determine the lack of specific clinical data points and automatically query the patient electronic medical record (EMR) to capture this data and integrate the data with the imaging dataset for final analysis.

If the technologist elects to perform quality assurance independently, then he/she reviews the combined image/clinical data and determines if the data is suitable for final interpretation. In this particular case, the technologist (Ms. Smith) detects minimal motion on one of the axial source imaging datasets and elects to incorporate a specialized image processing algorithm offered by the program 110, to minimize apparent motion. This can be done through an active visual command (directing visual gaze to the image processing icon and selecting (through eye tracking) the "anti-motion algorithm" from the pick list provided).

An alternative non-command based visual interaction could consist of focusing on a single image containing motion, which in turn prompts the program 110 to apply optional processing algorithms (in sequence) to the selected image. When the technologist identifies the optimized processing algorithm (i.e., best image quality), he/she adjusts their gaze, which in turn prompts the program 110 to apply that specific processing algorithm to the imaging dataset.

A hybrid approach would be to engage the automated quality assurance program function (see U.S. patent application Ser. No. 11/412,884) (through a visual command) on a specifically selected portion of the imaging dataset, and have the program 110 identify the optimized processing parameters for that specifically selected subset of images. The technologist could accept, reject, or modify the program 110 recommendations through a series of eye movements; which can also serve to adjust the magnitude of the image processing parameters utilized, using the program 110.

Once the imaging data has been optimized, the technologist is tasked with ensuring that the clinical data elements are optimized to facilitate interpretation. In this particular example of the chest CT angiogram for evaluation of pulmonary embolism, the technologist determines that several clinical and historical elements are missing, which impact the risk assessment for pulmonary embolism. These elements would include, for example, laboratory data (e.g., D-dimer, arterial blood gas), surgical and medical history (e.g., recent knee arthroplasty, history of ovarian cancer), medications (e.g., oral contraceptives), social history (e.g., smoking), and genetic profile. The technologist could manually search the EMR for this additional clinical data or instead elect to use intelligent agents of the program 110 to search the EMR for risk factors tied to the clinical diagnosis (pulmonary embolism).

This computerized search by the program 110 could be elicited by the technologist visually opening up the "Clinical Applications" profile, selecting the clinical diagnosis from an alphabetized list of diagnoses, and activating the "Search" tool. In addition, the technologist has the ability to edit the derived data based on direct interaction with the patient or family members and insert this edited information into the clinical data exam profile. Many of these same tasks can be streamlined and more efficiently performed using computerized thought recognition as described herein (once the technological advances have taken place) to allow mainstream applications within the medical domain.

As mentioned earlier in this text, a number of previously described inventions (see U.S. patent application Ser. Nos. 11/412,884 and 11/586,580, and U.S. Pat. No. 7,593,549) can be synergistically integrated with eye tracking and thought recognition for alternative computer navigation. Customized user-specific software can also be integrated with eye tracking to create a context and user-specific interface, based upon the individual preferences and skill sets of the individual user. The common theme is to create a customized human-computer interaction which can leverage automation as much as possible, and be supplemented by manual directives from the end-user in the form of visual input or thought recognition.

Figure 6:
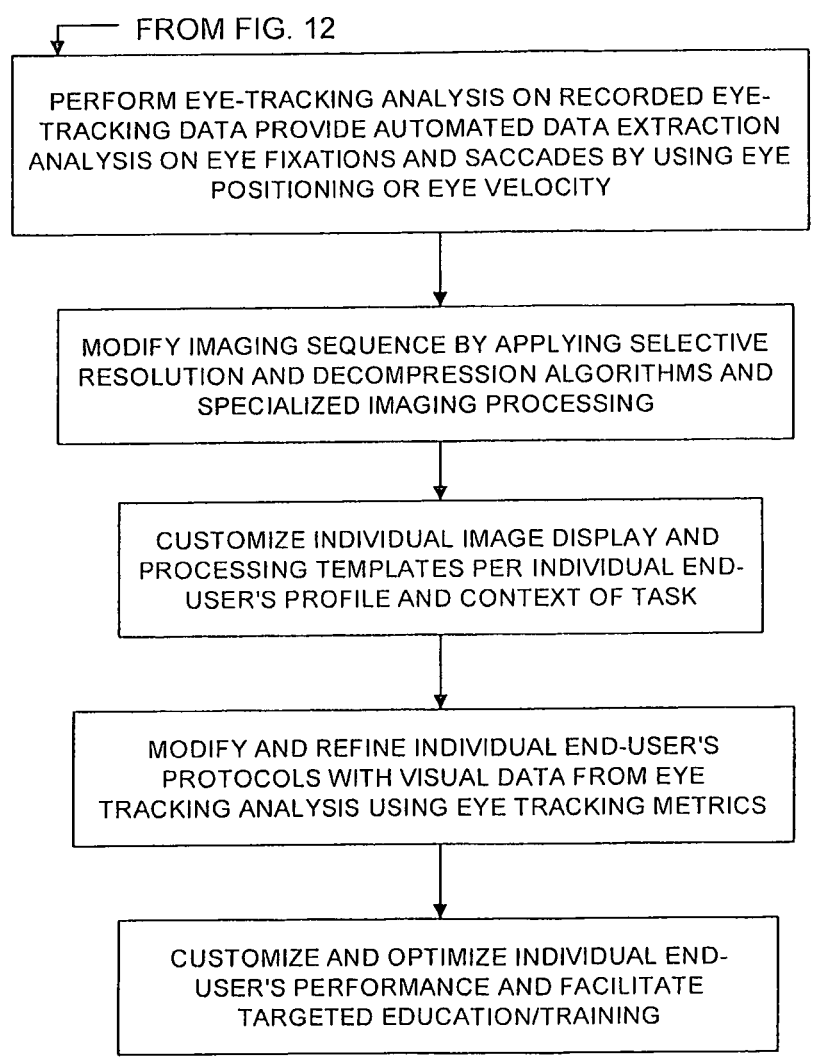
FIG. 6 is a flowchart showing the major steps in an eye-tracking analysis of a medical application, according to one embodiment consistent with the present invention.

Eye tracking analysis by the program 110 prospectively records the end-users' eye movements and retrospectively analyzes the recorded data (see FIG. 6, step 600). Further, the program 110 can be used to provide automated data extraction analysis on eye fixations and saccades by either using eye positioning or eye velocity. This provides information and knowledge as to "when, how, and where" eye movements took place. In turn this data can be used by the program 110 to derive "why", by determining the context in which the eye movement took place.

An example of how this eye tracking analysis can be used in real-time to assist the end-user performance in medical imaging would include selective resolution (both spatial can contrast resolution), as well as the application of decompression algorithms and specialized image processing by the program 110. In the case where a radiologist is reviewing a chest CT angiography in the evaluation of pulmonary embolism (i.e., blood clot in the lungs), the images may be displayed in a 4 on 1 format, so that the computer screen is divided into 4 compartments. In order to save memory within the archive or database 114 (for the 1,000+ individual images within the study), the exam may be stored by the program 110 at lower resolution and/or have compression algorithms applied. When the radiologists gaze is fixed upon a single image (e.g., upper left hand corner of the screen), the program 110 reacts to this visual data by selectively modifying the imaging sequence of interest in step 601. This could consist of the program 110 magnifying the image (switching from 4 on 1 to one on one display format), increasing the spatial resolution of that specific sequence of images, applying a decompression algorithm, or providing user and context-specific image processing. This latter example could consist of a simple task by the program 110, such as setting individual end-user window/level preferences, or something more highly specialized, such as image processing for a 3-dimensional display of the pulmonary arteries.

The individual image display and processing templates could be customized by the program 110, in step 602, in accordance with each individual end-users profile, for example (see WO 2007/145900, published Dec. 21, 2007, the contents of which are herein incorporated by reference in their entirety), and the context of the task at hand. In the cited example of the chest CT angiography for pulmonary embolism detection; the occupational status (e.g., technologist versus radiologist), specialty training (e.g., general radiologist versus sub-specialist interventional radiologist), and experience (e.g., radiology resident versus attending radiologist) would all be considered by the program 110 in the optimal image display and processing applications. In turn, the visual data derived from the eye tracking usability analysis would be used to modify and refine each individual end-user's protocols in step 603, so as to maximize visual performance (which can be measured through a number of eye tracking metrics.

Figure 7:
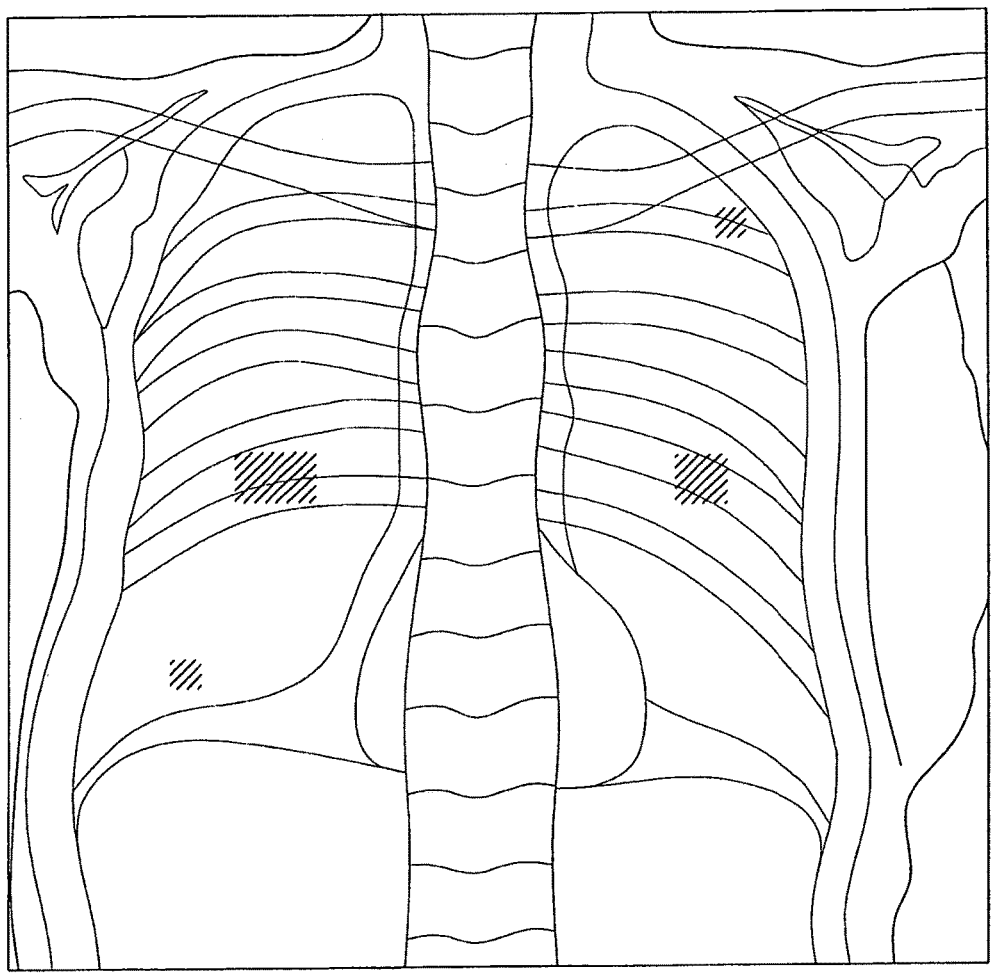
FIG. 7 is a diagram of a chest X-ray showing an eye-tracking apparatus and areas of visual interest, in a medical application, according to one embodiment consistent with the present invention.
Figure 7:
Figure 8:
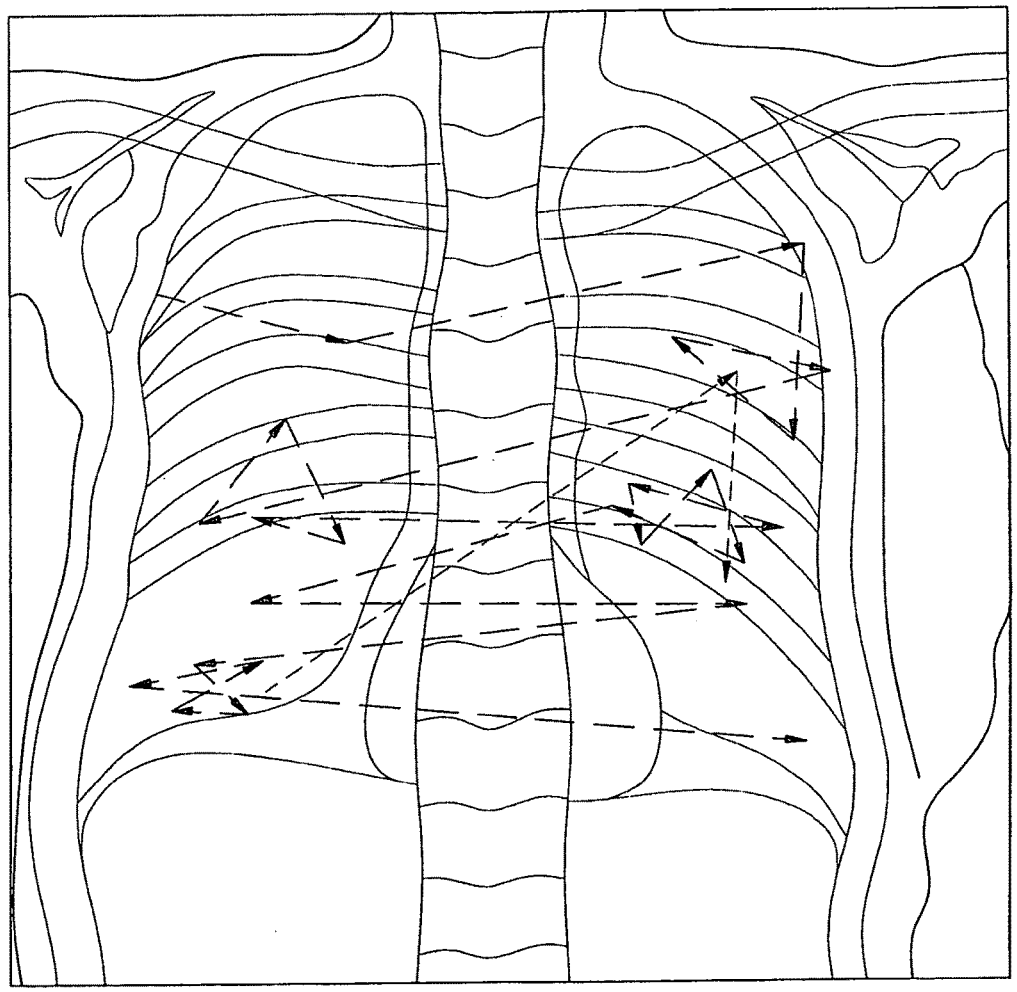
FIG. 8 is a diagram of a chest X-ray showing an eye-tracking apparatus with forward tracking and backtracking, in a medical application, according to one embodiment consistent with the present invention.
Figure 9:
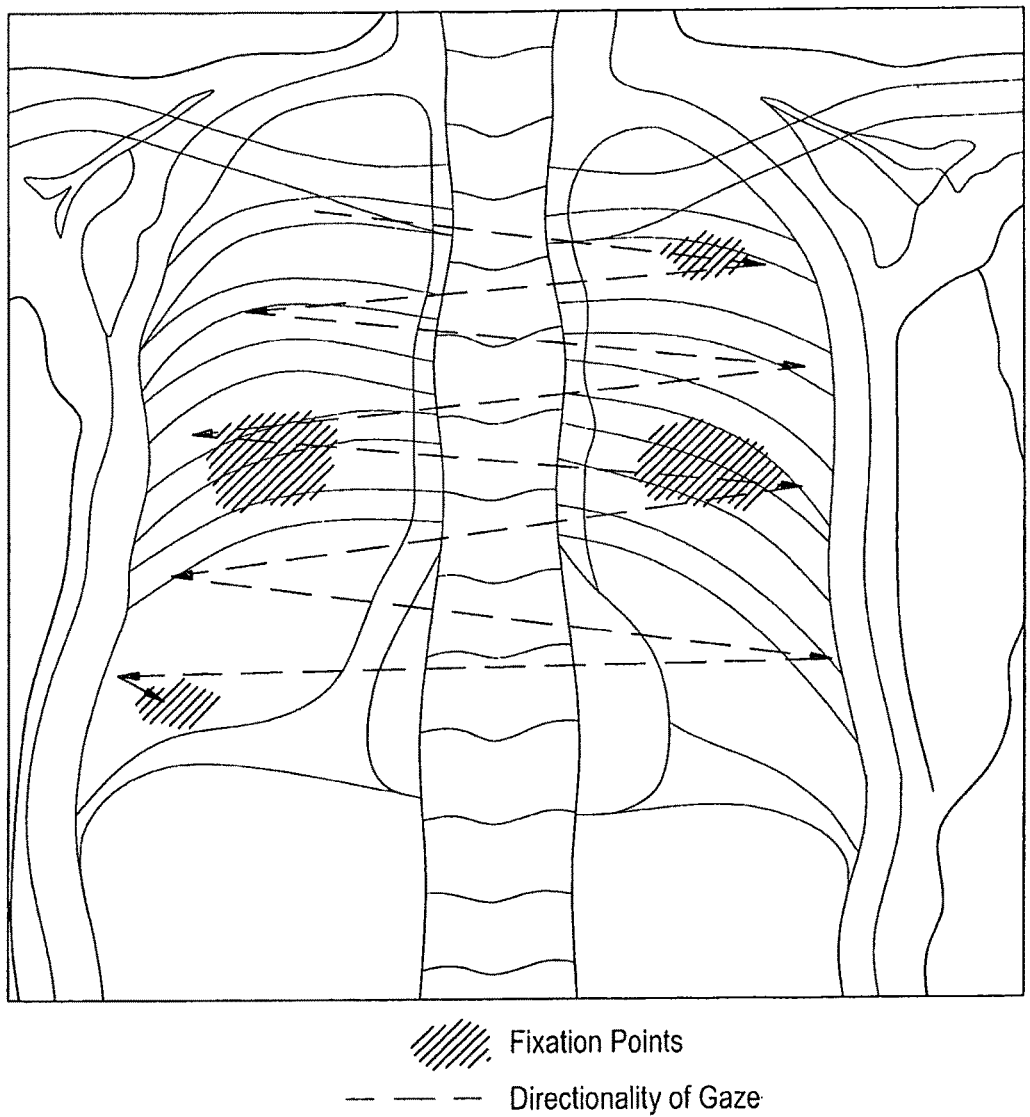
FIG. 9 is a diagram of a chest X-ray showing visual duration in an eye-tracking apparatus in a medical application, according to one embodiment consistent with the present invention.

The eye tracking metrics may include at least: 1) Gaze rate; 2) Gaze direction; 3) Gaze percentage; 4) Number of fixations, including a) Voluntary; and b) Involuntary; 5) Fixation duration; 6) Fixation rate; 7) Scan path directionality, including a) Length; and b) Duration; 8) Number of fixations over are of interest (AOI) (see FIG. 7); 9) Number of instances of backtracking (see FIG. 8); 10) Frequency of long duration dwells over AOI (see FIG. 9); 11) Saccade length; and 12) Fixation/saccade time ratio.

Figure 10:
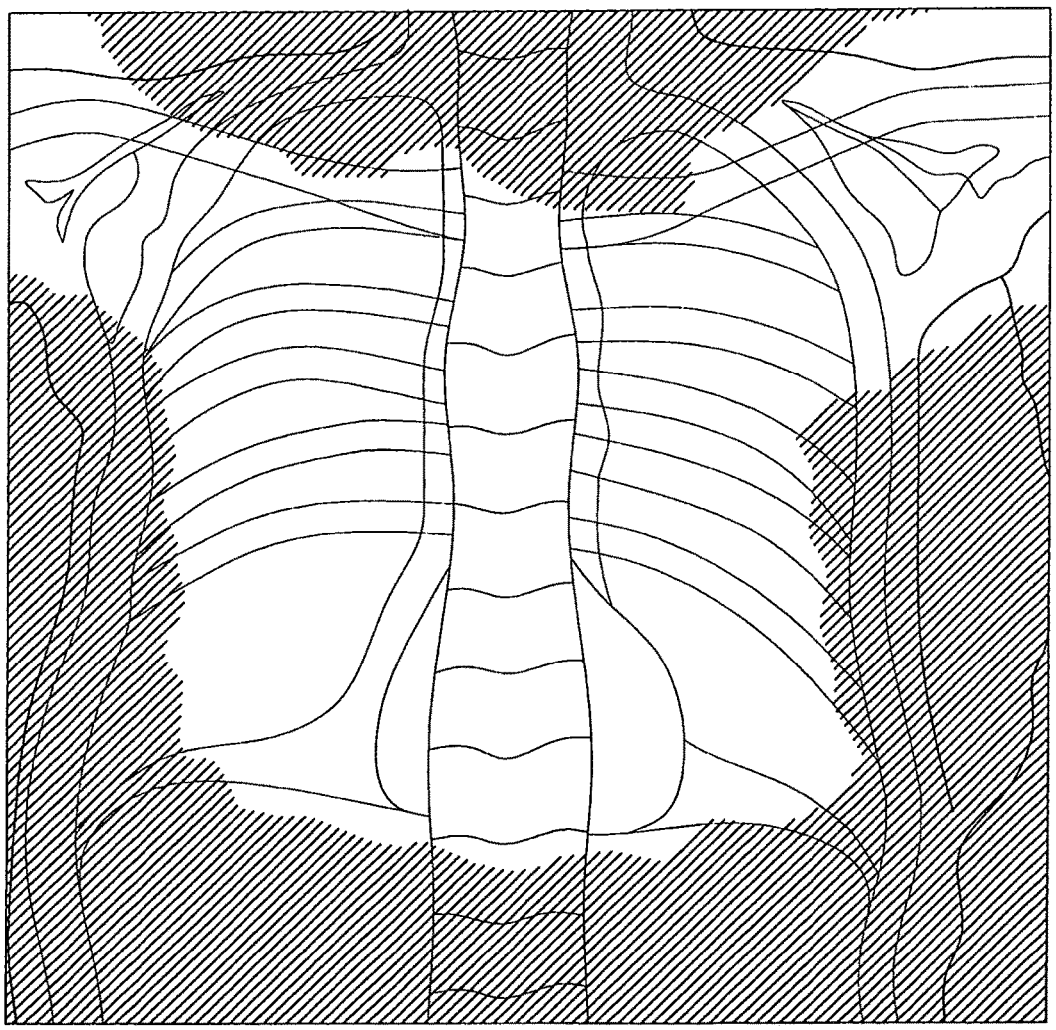
FIG. 10 is a diagram of a chest X-ray showing areas not visualized, in a medical application, according to one embodiment consistent with the present invention.

Fixation refers to stable eye position over a defined minimum time duration. Gaze duration (also referred to as "dwell") is the cumulative duration of a series of consecutive fixations within an area of interest (AOI). This AOI is a region within a visual display of particular interest. Scan path is a spatial arrangement of a sequence of fixations. Areas not visualized are shown in FIG. 10, for example.

The derived analysis of these eye tracking metrics by the program 110 can in turn be prospectively used to customize and optimize individual end-user performance and facilitate targeted education/training. As an example, in the same example of a CT angiography of the chest (for evaluation of pulmonary embolism), with three different end-users (each of which are radiology residents in training), the program 110 will perform an analysis of eye tracking performance to evaluate the following metrics: 1) Number of fixations (voluntary and involuntary); 2) Number of fixations over AOI; 3) Number of instances of backtracking; and 4) Scan path directionality (length and direction).

The three end-users are: Resident A in his first year of training, with very little experience and knowledge of chest anatomy, pathology, and angiography; Resident B in her third year and whom is quite familiar with chest anatomy and pathology, although with limited experience with the specifics of angiography; and Resident C, a fifth year resident, who has extensive knowledge and experience with all aspects of chest imaging, and whom has even had subspecialty training in angiography. The eye tracking analysis by the program 110 for Resident A, B, and C is summarized as follows:

Resident A: excessive number of involuntary and voluntary fixations, with a large number of backtracking and unpredictable scan path directionality.

Resident B: high number of voluntary fixations over AOI, with a few backtracking and prolonged length of expected scan path directionality.

Resident C: highly focused and limited number of fixations over AOI, minimal backtracking, highly focused and predictable scan path directionality of relatively short duration.

Based upon these analyses by the program 110, one can see that the eye tracking efficiencies of the three residents are proportional to the length of training and relative experience. As a result of this data, the program 110 can create different customized visual profiles for each of the three residents, in an attempt to maximize visual efficiency relative to their individual eye tracking patterns. For resident A (little experience and inefficient eye tracking), the program 110 can promote more efficient eye tracking patterns by creating "visual fixation maps", which are highlighted areas within the imaging data which have been shown through longitudinal eye tracking analysis of large reader groups to be areas of intense and reproducible interest to the task at hand and specific imaging dataset. In this particular context (i.e., evaluation of pulmonary embolism) and imaging dataset (i.e., CT angiography); the visual fixation maps provided by the program 110 highlight the first, second, and third order pulmonary arteries in both the axial 2-D images and 3-D reconstructions. This can be done by the program 110 in several different ways, through the incorporation of color maps (superimposed over the pulmonary arteries), magnification of the selected anatomical structures, or segmentation of the pulmonary artery branches on sequential images.

When Resident A's eye tracking analysis performed by the program 110 demonstrates fixations outside the AOI, a visual or auditory cue (e.g., blinking light) can be provided by the program 110, alerting him as to inefficient eye tracking. When the dwell times exceed a pre-defined threshold, a different alarm (i.e., ringing sound) may be engaged by the program 110, thereby alerting him to the excessive dwell time. The eye tracking analysis is then recorded by the program 110 as to the proportion of efficient versus inefficient eye tracking for the given task at hand. This analysis is repeated over time, so that a longitudinal record visual eye tracking efficiency of Resident A is presented (in graphical format) for review.

If this analysis by the program 110 shows, for example, that the visual feedback cues have resulted in a 40% decrease in fixations outside the AOI, but only a 10% decrease in dwell time duration, then the program 110 may issue a prompt to both the resident and his supervisory attending radiologist, recommending certain educational programs for remedial training. This may consist of an on-line anatomy atlas to review pulmonary arterial anatomy or a teaching file casebook of positive and negative pulmonary emboli. The object of the exercise is to utilize the eye tracking analysis of each individual end-user to maximize visual performance and efficiency.

For resident B (intermediate experience), the eye tracking analysis performed by the program 110 has shown good visual performance with the conventional 2-D imaging datasets, but inefficient eye tracking (e.g., excessive fixations over AOI) on the 3-D specialized reconstructed datasets. The program 110 provides feedback to Resident B and offers a number of proactive solutions to improve performance. The first is to present all imaging data in the 2-D (conventional) format for the default visual display templates, and reserve the specialized 3-D images only for those cases in which it is specifically requested. (This can be done by having Resident B invoke the 3-D application by gazing at the 3-D image processing icon displayed on the toolbar). The second recommendation is to provide Resident B with a computerized educational program reviewing the fundamentals of CT angiography and the 3-D image processing applications available (along with a few test cases). The third option is to automatically invoke the 3-D application only for those cases perceived as positive. This can be inferred when Resident B's gaze is prolonged over a specific region within the AOI, which would suggest the presence of pulmonary embolus. In the event that the pre-defined threshold is reached, the specific region of interest (e.g., third order branch of the right lower lobe pulmonary artery) is targeted with 3-D reconstructions. This selectively targets the anatomic region of interest and limits the imaging volume required for visual analysis. For each different method employed, the eye tracking analysis by the program 110 will longitudinally analyze end-user performance over time, in order to provide feedback and make recommendations as to the most efficient method of intervention.

For resident C (the most experienced) the eye tracking analysis by the program 110 demonstrates high levels of efficiency using all available applications. The eye tracking analysis places Resident C in the category of "sophisticated and highly efficient user". In doing so, the program 110 will correlate Resident C's data with that of similar users in this category and provide recommendations based upon what "best practice" guidelines of comparable "sophisticated and highly efficient" users. Suppose a new image processing application was made available for this exam type (CT angiography) and context (pulmonary embolism). The eye tracking analysis by the program 110 within this selected group reported a 10% improvement in visual efficiency (e.g., gaze rate and direction) using this new processing algorithm and prompted Resident C with the recommendation of incorporating this new application into his default processing parameters. In another example, the eye tracking analysis by the program 110 could identify a specific radiologist (Radiologist X) within this peer group with the highest visual performance scores and offer to Resident C the option of incorporating Radiologist X's automated visual display templates into his own. The idea here is to provide end-user's with the ability to "test drive" visual display/processing templates from other end-users with similar profiles and higher visual performance scores.

Another feature of the integrated eye tracking usability analysis is the ability of the program 110 to incorporate other ocular performance metrics, indicative of visual fatigue (e.g., blinks, convergence, and accommodation). When an individual end-user's measures exceed baseline, a visual or auditory prompt can be provided by the program 110, alerting the end-user of higher than normal levels of visual fatigue. The end-user can then have the option to:

1) Continue "as is".
2) Incorporate anti-fatigue measures.
3) Take a rest.

If the end-user elects to continue "as is", the program 110 will continue to monitor these stress measures of ocular performance and mandate action (e.g., mandatory time out) in the event that a critical threshold has been reached. This data (including the ocular performance metrics, computerized alerts, and actions taken) are all recorded in the eye tracking database 113, 114, by the program 110, for future review. An end-user who has demonstrated poor clinical performance (e.g., diagnostic accuracy) may be forced to have visual restrictions imposed to ensure optimal performance. Visual anti-fatigue measures by the program 110, could include alteration in monitor brightness, image display format, navigational speed, or image processing.

Eye tracking usability analysis by the program 110 can also be used to optimize eye tracking input. For example, an individual end-user may select a user interface (UI) which employs a series of icons on the toolbar (which is displayed in a horizontal fashion on the top of the computer screen), which are used for eye tracking input. If the end-user double blinks over the magnification icon, then this function will be activated by the program 110. The end-user can then de-select the magnification icon and activate the zoom and scroll function by subsequently double blinking over this icon. In the eye tracking usability analysis, visual inefficiency is observed through an excessive number of extraneous toolbar fixations. As a result, it is determined by the program 110 that visual performance can be improved by altering the UI by replacing the toolbar icons from the top to the side (in vertical fashion) and changing the order of individual icons. Subsequent analysis by the program 110 shows a reduction in extraneous fixations and this is then used as the new user interface (UI).

The derived eye tracking data which is recorded from each end-user's human-computer interaction creates a series of objective data, which in turn can be downloaded into a visual database 113, 114 by the program 110. This database 113, 114 in turn can be used for clinical and basic science research, development of optimized (i.e. best practice) guidelines, development of new technologies (related to the human-computer interaction), and customized education and training programs. The goal is to rebalance the human-computer interaction in a way that optimizes and economizes end-user input, in a context and user-specific fashion.

A number of applications can be derived from the invention. In a manner similar to the functionality of a manual input device, such as a multi-programmable mouse, a series of eye tracking commands can be created to define specific commands, such as creation of a report, navigation through a dataset, selection of workstation tools, or activation of specialized computer-based software programs. These eye tracking commands can be universal in nature, or customized to the specific preferences of the individual end-user. In either case, an eye tracking command profile is created which can be directly applied based upon the individual end-user's authentication (using Biometrics, as in U.S. Pat. No. 7,593,549). With the creation of local, regional, and national eye tracking databases 114; this user-specific eye tracking command profile can be accessed whenever the end-user signs onto a computer 101.

In addition to creating user-specific eye tracking commands, the eye tracking commands can also be tied directly to the context of the human-computer interaction. As an example, the eye tracking commands utilized in reviewing a chest CT scan for evaluation of lung cancer might be different from the eye tracking commands used for reviewing a brain MRI for stroke.

As the visual database 113, 114 matures, statistical analysis by the program 110 can reveal those common actions (i.e., visual commands) which are predictably repeated by the individual end-user, as well as his/her peers, for the individual task at hand. This analysis could in turn lead to the creation, by the program 110, of automated visual command templates (a derivative of the automated workflow templates as in U.S. patent application Ser. No. 11/586,580). The individual end-user could in effect turn on and turn off these automated visual command templates through the course of their workflow and revert to manual visual workflow through a single visual command.

The statistical analysis of the visual database 113, 114, by the program 110, could also derive the most efficient patterns of use and in turn use these for creating "best practice" automated visual command templates. These "best practice" visual command templates could be used in the creation of educational/training programs to educate end-users (based upon their individual profiles and each specific task being performed) as to the most operationally efficient visual workflow.

In addition to the "best practice" visual command templates, another way of the program 110 providing feedback to each individual end-user can come in the form of a feedback function, which assesses the efficiency of each end-user during a specific exercise. As an example, a radiologist interpreting a brain MRI for stroke, could have the eye tracking analysis from that particular exercise correlated by the program 110 with the eye tracking data from his/her individual visual database 113, 114 from similar actions. If in this particular case, the radiologist was shown to have an excessive number of instances of backtracking; the program 110 derived analysis could provide this feedback to illustrate to the end-user the additional backtracking which took place.

Another embodiment of this user-specific feedback function would include an electronic timer within the program 110, which monitors certain actions and provided instantaneous feedback. For example, a radiologist becomes fixated on a certain region of the chest radiographic image he was reviewing. After a pre-defined period of time, the program 110 could provide an auditory prompt to the end-user, alerting him/her as to the fixation, in an attempt to encourage a more efficient visual search of the image. At the same time, if program 110 based analysis of the visual search demonstrates that certain portions of the dataset were not searched (i.e., reviewed), the program 110 could provide a prompt to the end-user, highlighting the specific region not analyzed. In the case of a mammogram being reviewed by a surgeon, this could consist of an entire image not viewed, or a specific area (e.g., subareolar region) on a single image.

The feedback function of the eye tracking analysis can also be used to create a data repository 113, 114 for future review, education, and training. At the completion of each task (e.g., interpretation of an x-ray), the annotated image showing a compilation of the visual data mark-up is stored by the program 110. In the event that inefficiencies in eye tracking were identified (e.g., excessive fixations), the areas of deficiency are distinctly marked (e.g., color coded) by the program 110 for easy identification on future review. This repository 113, 114 can be reviewed at a later time with educational pointers defined for optimal performance. Thus, an end-user can search the repository for his/her own analysis, or other end-Users' analyses.

In one example, a radiology resident in training may want to compare his/her own analyses of chest radiographs (for lung cancer screening) with those of more proficient end-users. The resident could open up the teaching application (e.g., through activation of the teaching application icon on the toolbar using visual input) and select the specific function he desires (e.g., visual input from a pool-down menu). If he/she selects the comparative review function, and then selects the modality, anatomic region, and context (e.g., chest radiograph, general screening), the teaching function of the program 110 will then present representative examples of his/her own visual analyses (marked up on radiographs he/she previously reviewed) and then compare them with a "high efficiency" reader. In addition to presenting the resident with the individual visual map images, the program 110 could also render subtracted images, highlighting specific areas of inefficiency. The resident can then invoke the "practice" function of the program 110. In this case, the program 110 will present the resident with a series of practice images and record their visual search patterns, providing feedback as to how the practice search patterns compare with their own prior visual search analysis and those of the "high efficiency" reader. In doing so, a simulation program 110 can be created utilizing statistical analysis of the visual database 113, 114 with identified areas of potential improvement by the program 110. One could even go so far as to create a video game model where points are recorded (both positive and negative) for efficient and inefficient visual analysis.

The same approach can be taken for the alternate visual input command function. In addition to analyzing visual search characteristics (for image review/interpretation), the program 110 can also analyze the visual command characteristics. In this case, the program 110 records the efficiency of visual input commands and provides feedback to the end-user as to operational efficiency. In a similar manner, this data can be stored by the program 110 in a separate visual database 113, 114 (i.e., for visual input commands), and undergo statistical analysis with education options by the program 110. The purpose of such a system is to create an iterative learning tool to promote optimal efficiency as well as improved customization (e.g., user interface).

The relationship between visual performance (both for search and input) can also be correlated with the end-user's emotional state (e.g., stress) and fatigue (e.g., accommodation). This creates an additional point of data analysis to assess visual performance, which can be correlated by the program 110 with the individual end-user's profile. As an example, two (2) different radiologists, each of which has similar training and experience are considered. Radiologist A is a "type A" personality, who experiences a great deal of baseline stress. Radiologist B is a "type B" personality, who adapts easier to external stressors and has a calm demeanor. Both radiologists have efficient and similar visual search and command profiles. However, during the course of a given day, as exam volumes begin to increase, Radiologist A begins to experience increased stress (as measured by affective computing, such as galvanic skin response), whereas radiologist B remains relatively stress-free. As Radiologist A's stress levels begin to reach a certain threshold, the program 110 identifies new inefficiencies in both visual search and input command analyses. The program 110 provides feedback to Radiologist A regarding this divergence in visual performance relative to his baseline and offers a number of options:

1) Continue reading "as is".
2) Activate the automated visual display templates.
3) Take a short break.
4) Turn on pre-selected background music.

Regardless of which option is selected (through visual input command), the program 110 continues to analyze visual performance. If a critical threshold in visual performance degradation is reached, a mandatory time out may be instituted by the program 110.

Radiologist B does not incur any increase in stress as exam volume increases, but does slowly begin to demonstrate measures of increased fatigue (e.g., measured by visual accommodation). The analysis by the program 110 is presented to Radiologist A, with a similar list of options. In both examples, there is an interactive component of computerized visual performance analysis, coupled with stress/fatigue measurements, and interventions. The goal is to provide objective feedback to the end-user, which takes into account different user profiles and intervention measures.

Another feature of the present invention is the ability to not only review imaging data, but also to use visual input commands to generate a report. Using reporting functions, for example, Gesture-based Reporting icons (see U.S. Pat. No. 7,421,647), displayed on the reporting toolbar, the radiologist can input visual commands while searching the image to generate a report. The sequence of events is described below:

1) Radiologist selects desired case from worklist.
2) Radiologist scans image.
3) Program 110 highlights areas of visual fixation (as potential areas of interest).
4) Radiologist identifies each individual AOI.
5) After fixating on one specific region (e.g., heart), the radiologist selects from the reporting toolbar the icon for that specific finding (e.g., cardiomegaly).
6) Additional finding-specific descriptors or modifiers can be inserted into the structured text report and annotated image, by visually selecting these items from the reporting menu options (e.g., severe, interval increase).
7) The radiologist then fixates over the second AOI and repeats the same process.
8) In the event that a radiologist does not want to incorporate a certain AOI into the report, he can do so by either ignoring it or selecting the delete reporting option while fixating over the AOI.
9) The radiologist can go back to any AOI (i.e., report finding) and edit at any time.
10) When finished the radiologist simply issues a visual input command for "Accept and sign report".

In addition to report creation, visual input commands may be used by the program 110 for activating other computer-based functions, such as decision support. As an example, a radiologist reviews a mammogram and wants to activate the computer-aided detection (CAD) software. This can be done a number of different ways including (but not limited to) activating the CAD icon from the toolbar, or inputting a CAD-specific visual input command. In addition, the program 110 can issue a prompt to ask if the radiologist desires this function based upon visual search analysis. The radiologist may dwell over a region containing micro-calcifications within the breast (which will be annotated as an AOI) and then may visually backtrack to return to this same region a few seconds later. The program 110 may recognize the diagnostic uncertainty posed by this visual search pattern and prompt the radiologist with the option of activating CAD. The radiologist can respond with a "yes" or "no" visual input command. In this manner, activation of decision support applications can be initiated by the end-user (through an active visual command) or activated by the program 110 (though a passive visual command). The visual analysis database 113, 114 can record these events and refine the process by identifying those search patterns associated with CAD activation and those without. On subsequent events, the information garnered, will be used to customize which search patterns individual end-users use prompting the activation of a specific program and which do not. This data will also be used by the program 110 to update and refine the automated visual search templates.

Another application (apart from decision support) which can be driven through visual input commands (and distinctive visual search patterns), is data extraction and mining of databases 113, 114. In addition to mining of the visual database 113, 114, other database searches (e.g., report database, teaching file database) may be activated through a visual input command. As an example, a radiologist reading the mammogram with micro-calcifications may be interested in learning if the patient has any clinical risk factors which would increase the risk of these micro-calcifications being malignant. The radiologist, after identifying the visual AOI and finding (micro-calcifications), may invoke the "clinical data search" application through a visual command. The clinical database 113, 114 within the patient's electronic medical record (EMR) could then be automatically queried to identify any clinical risk factors which may be relevant to the recorded finding (breast micro-calcifications). The automated search of the EMR clinical database 113, 114 by the program 110, may identify the following data points (which serve to improve his ability to render a diagnosis):

a) genetic marker for breast cancer (BRCA);
b) family history of fraternal breast cancer;
c) benign breast biopsy contralateral breast.

Another method of data mining would include invoking the finding-specific image repository. The program 110 could then automatically retrieve all stored cases of breast micro-calcifications with similar visual and report features and present them to the radiologist. Those with pathology correlation (based upon biopsy results) can be visually compared against the current AOI to assist in the characterization of these micro-calcifications.

Figure 11:
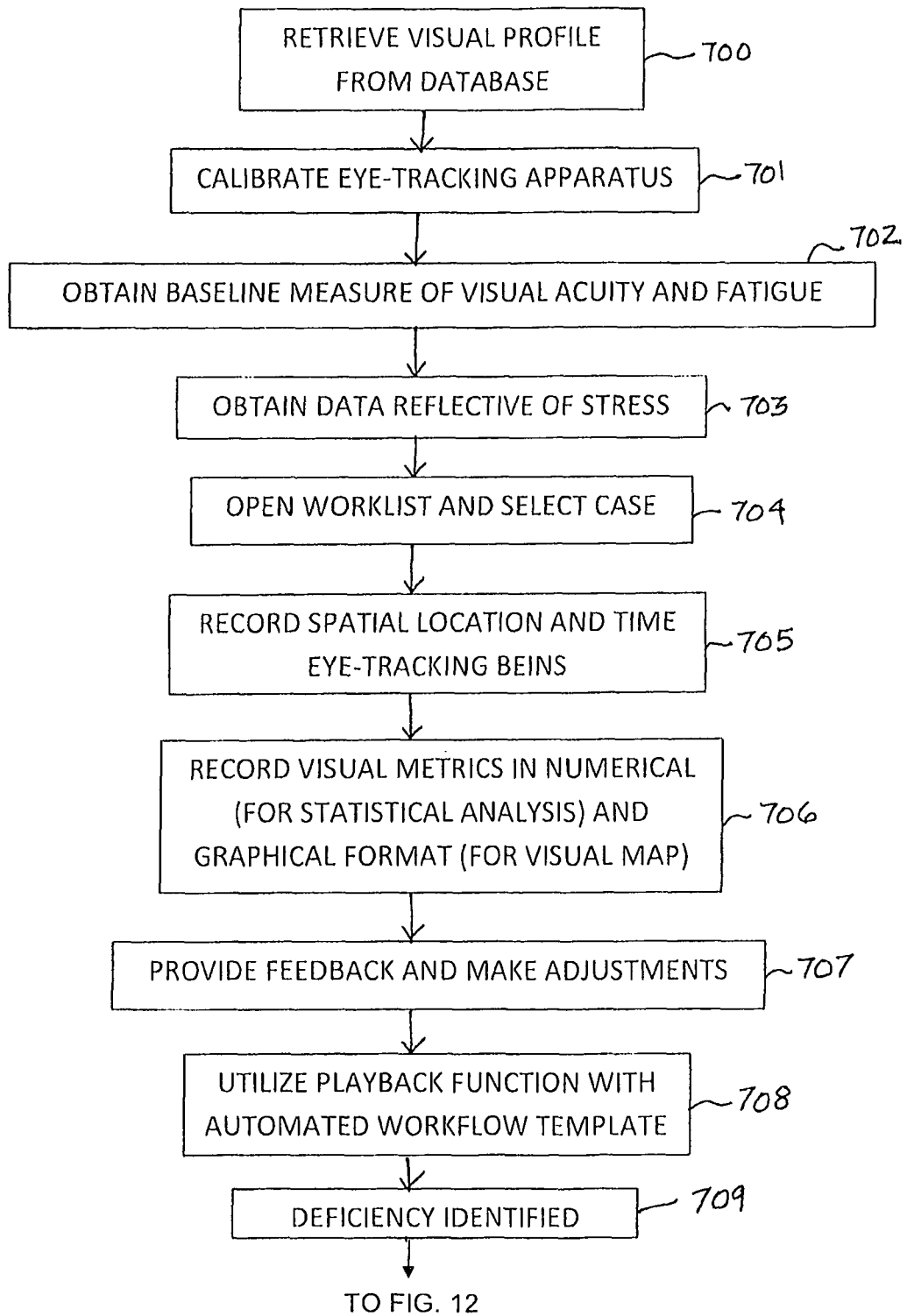
FIG. 11 is a flowchart of steps in a method of utilizing an eye tracker in a medical application, according to one embodiment consistent with the present invention.

In one embodiment, the present invention includes an eye tracking device 300 directly integrated into the computer monitor 102. After the end-user has logged onto the program 110 and been authenticated (using Biometrics, for example), his/her visual profile is automatically retrieved from the database 113, 114 by the program 110 in step 700 (see FIG. 11). This user-specific visual profile would include a number of parameters including (but not limited to) occupation, experience, visual acuity, historical record of eye tracking analysis, and visual input command preferences.

Before imaging data is presented to the end-user by the program 110, a calibration step in step 701, is required to ensure that the visual eye tracking equipment is appropriately calibrated. This would include a 3×3 dot array, where the program 110 prompts the end-user to fixate on each individual dot and the program 110 adjusts calibration accordingly. In the event that the calibration exercise was to fail, recalibration would be required.

In step 702, a baseline measure of visual acuity and fatigue is obtained by the program 110. A number of different visual acuity tests are available (including the classic eye chart). Visual fatigue measures can be accomplished using an autorefractor, for example.

Once calibration of the eye tracking apparatus and visual fatigue measures have been completed, an optional step 703, is to turn on the affective computing program 110, which collects data reflective of stress. The combined eye tracking, visual fatigue, and stress-related data will all be recorded by the program 110 in individual and combined databases 113, 114 to assess the individual and collective impact these variables have on end-user performance. A number of affective computing technologies are readily available (e.g., galvanic skin response, facial expression software, blood pressure and pulse, etc.), for the program 110 to record a baseline stress measure prior to initiating work.

Note that these calibration, visual acuity/fatigue, and stress measures would be repeated at regular (e.g., hourly) intervals during the course of a prolonged read-out.

Once these calibration and baseline data have been collected, the end-user can begin work. In the case of a radiologist, the unread worklist is opened and a specific case is selected in step 704. The opening of different applications and cases are done through visual input commands. In particular, the radiologist would select the desired case by double blinking and the case would be opened onto the computer screen 102.

Each image would have a designated starting point (e.g., red dot at the 12 o'clock position of the image), which allows for the eye tracking analysis by the program 110 to begin. Both the spatial location and the time eye tracking starts, would be recorded in the corresponding database 113, 114 in step 705.

As the end-user scans through the imaging data, the eye tracking device 300 records a number of visual metrics in step 706, which are simultaneously recorded in two formats by the program 110: numerical and graphical. The numerical data is used for statistical analysis, while the graphical data would, in effect, create a visual map which illustrates the sequential events overlaid onto the image being reviewed. Each recorded data point would have a beginning and end time to calculate dwell times and identify specific areas of (visual) interest (AOI).

As the end-user tracks through the imaging dataset, he/she may also elect to manually input visual commands to assist in image analysis, performed later. This could take the form of workstation tool usage (e.g., magnification, measurement, and scroll), or activating additional applications (e.g., image processing, report creation, and decision support).

The visual maps created may include eye tracking alone, visual inputs alone, or a combination of the two. The derived eye tracking map presented by the program 110 would show point by point the eye tracking which occurred during the course of each image review. The visual input map would graphically show each input command in chronological order. The combined map would be a composite of the two, so that one could literally have the ability to re-create the entire scenario of what and when the end-user did in reviewing and analyzing the imaging data. As previously stated, all of these recorded data points would have corresponding time stamps to show the duration of each action. These steps would be repeated for each individual image, reviewed within a multi-image dataset.

Of course, feedback to the user would be provided in the event of fatigue or stress-related cognitive impairment, and adjustments made by the program 110 or the user, in step 707.

In the event that the user would like to move along more quickly in the sequence of review, a playback function could also be created by the program 110 in step 708 using this combined eye tracking and visual input data to literally cycle through the entire exercise in the identical manner in which the end-user has performed the function (or other end-users have performed a similar function). This would be analogous to the automated workflow templates, but in this case represent an automated visual workflow template.

In the event that the data analysis by the program 110, in step 709, identifies deficiencies in the eye tracking analysis (e.g., region of the image not reviewed), an alert will be provided to the radiologist by the program 110 in step 710 (see FIG. 12), with a graphical representation of the deficiency. In the case of "missed imaging data", the radiologist would be presented with the image along with a region of interest highlighting the area of deficiency.

Once all images have been satisfactorily reviewed and any additional actions (e.g., report creation) completed in step 711, the radiologist will issue a visual command for completion, storage, and closure of the exam in step 712. Thereafter, image analysis and eye-tracking analysis are performed in step 713, in accordance with the steps shown in FIGS. 3 and 6, for example.

In the event that the radiologist opts to open a new case, the case will be selected from the worklist and the exercise will be repeated.

In additional applications, similar to its application in medical imaging analysis, the present invention can also be used for non-imaging medical documents. The manner in which an end-user visualizes data contained within a text-based or numerical data display can also be analyzed through eye tracking analysis, and have input commands through eye input. As an illustration, the examples of a consultation note and laboratory report are used.

For the consultation note, as the end-user "reads" the text-based document, the program 110 records the same visual metrics previously described and records this analysis in the corresponding database 113, 114. The end-user is then presented by the program 110 with the eye tracking analysis of this document visual search, with highlighted areas of fixation, which serve as potential areas of interest. Using this "highlighted" analysis or using the original document, the end-user can use visual input commands (e.g., double blink) to select "key data points", which can then be transferred to a patient/context specific folder, within that specific end-user's database.

As an example, a primary care physician (Doctor Smith) may be reading a cardiology consultation and identifies several areas of interest within the document:

1) EKG findings.
2) Recommendations for additional cardiac testing.
3) Adjustment of medications.
4) Using his/her pre-defined visual input command for "save data", Doctor Smith, identifies each data element and directs the specific folder in which the data will be recorded. For "EKG findings", Doctor Smith selects two (2) different folders for the data to be stored:
5) Test results.
6) Master medical record data file.

The specific folders are selected by visual input from a list of options, which can be accessed from the toolbar, icons on the desktop, or a pull-down menu. In certain cases of high frequency use (e.g., master medical record), Doctor Smith may have a specialized visual input command (i.e., shortcut), which precludes the need to identify the folder from the toolbar. The EKG findings are then transferred by the program 110 to the corresponding data files within the patient-specific database, time stamped, and identified as to the data source. These additional data elements are used in future data mining analysis.

The same steps are taken for the other data points of interest. For "additional cardiac testing", in addition to data storage, Doctor Smith also selects the "Place Order" option within the electronic medical record (EMR), which electronically orders the recommendations using the program 110. Once the order has been successfully completed, electronic alerts are sent to all parties by the program 110, including the consulting cardiologist, ordering physician (Doctor Smith), and the patient.

A similar pathway is taken with the "Adjust Medications" data. In this case, a slightly different function can be illustrated based upon the additional input of the pharmacologist and/or Doctor Smith. Suppose for example, the consulting cardiologist recommended an adjustment in dosage of one drug, discontinuation of another drug, and addition of a new drug. Before electing to do this as recommended, Doctor Smith elects to consult a pharmacologist. The consultation tied to this data can also be performed through visual input commands through the following actions:

1) Doctor Smith selects the data of interest.
2) Doctor Smith selects the data files in which this data is to be transferred.
3) Doctor Smith also issues an additional order for "Consultation" through visual input commands and selects the consultant requested (e.g., from a pull-down menu).
4) Doctor Smith may also insert a brief note for the consulting pharmacology consultation requested through visual input by using a letter keypad with visual input. This can be done by simply selecting the letters (e.g., registered through length of gaze).

In the example the consulting pharmacologist identifies a potential adverse drug interaction between the existing drug regimen being taken and the new drug recommended. The pharmacologist then issues a consultation note (in a manner similar to the cardiology consultation), and this is sent by the program 110 to the consulting cardiologist and Doctor Smith. In this case however, the pharmacologist has created visual "key data" highlights within the consultation note, by pre-selecting certain portions of the consultation note as "key data". This can be visually displayed in a number of different ways by the program 110 (which can be customized to each individual end-user's preferences). Doctor Smith has defined these highlighted data points to be visually displayed in a different color schema (based upon different levels of urgency), while the cardiologist has defined the highlighted data points to be displayed in combined bold/italics font. By creating the consultation note using pre-selected highlighted areas, the pharmacologist has pre-defined "areas of interest" for the visual analysis and feedback function. This functionality makes it mandatory for the end-user reviewing the data to visualize and formally acknowledge data review. This can be done in a number of ways, including (but not limited to) an active visual input command (e.g., two (2) blinks) or a passive input command (e.g., prolonged gaze). If the end-user reviewing the data did not have acknowledged data review, the program 110 would display the highlighted data points and request formal acknowledgement before proceeding to another task.

Once Doctor Smith acknowledges receipt of the pharmacologist data, he then proceeds to the "Medication Order" function. Doctor Smith can input new orders by inserting the order manually, or by "cutting and pasting" an order from another data source (i.e., pharmacologist consultation note). In the event he elects to visually enter the order from the "cut and paste" option, the order confirmation will be sent to all parties involved, by the program 110, with the data input (Doctor Smith and consulting pharmacologist). In addition, Doctor Smith can select for this order to also be sent to a third party (e.g., consulting cardiologist, patient) by "copying" this data and identifying the party of interest. All data is recorded by the program 110 in the appropriate databases 113, 114 (user and context specific) for documentation and future analysis.

Another important function of the eye tracking analysis for medical documentation is the ability to record and provide feedback as to what specific data points are reviewed and which data points are omitted from visual inspection. As an example, an end-user only reviews the "Impression" of a report document and failed to visually review the "body" of the report. The visual analysis feedback will be presented by the program 110 to the end-user, and the program 110 will issue a warning which highlights which data components were not reviewed (in a manner similar to the visual analysis of the medical imaging showing which anatomic regions were not visualized). The end-user can then elect to continue without visual review of the "not reviewed" data, or review the identified area of interest. All visual workflow steps will be recorded in the end-user and context specific visual databases 113, 114 by the program 110.

The derived data presents unlimited opportunity for research and "best practice" analysis. As an example, different visual analysis patterns are analyzed by the program 110 from a large pool of similar end-users and correlated with clinical outcomes. In our example, the radiologists' interpretation of the mammograms are correlated by the program 110 with visual search patterns of these radiologists with their positive and negative predictive values (which is data currently mandated for collection and analysis through the Mammography Quality Standards Act (MQSA)). Based on this combined "visual" and "clinical" analyses, it may be determined by the program 110 that certain eye tracking patterns are associated with higher clinical performance measures. This data analysis can in turn be used by the program 110 to provide user-specific analysis and development of optimized automated visual display templates for mammography interpretation.

The present invention is not only restricted to medical applications, but can also be used for a variety of other computer-based visual applications. Any time an end-user is on the Internet, he/she is visually "surfing", as they quickly navigate through a variety of web pages and URLs. In the process of doing so, they are visually assimilating data in an electronic format. Using the same eye tracking analysis principles, the program 110 can assess exactly what data is and is not being reviewed, the duration of visualization, and the efficiency of eye tracking. The analysis of this computer-based visualization analysis by the program 110 can be shared with the end-user for education/training, as well as provided to the Internet content provider to educate them as to how the data being presented is being reviewed.

In addition to a detailed eye tracking analysis, which shows directionality, fixations, and backtracking, a simplified analysis can be created by the program 110 each time a viewer accesses a webpage—which could consist of a color mapping superimposed over the Internet page layout to illustrate the location and duration in which data is being reviewed—and the program 110 can correlate it with the individual end-user's profile to better understand which types of data (i.e., content) are preferable, the optimal manner of data display (e.g., graphical, textual, color coded, etc.), and the optimal data layout (i.e., location) for different types of end-users.

Using the end-user profiling and visual eye tracking data (each of which is recorded and analyzed in their respective databases 113 114 by the program 110), customized data display templates can be created, so that upon signing onto a URL, the content provider could customize the data display in keeping with that particular end-user's profiles. Simplistically, this could include a series of visual display templates options (from which the optimal "match" is selected for presentation by the program 110), or evolve into something far more complex, where standardized data is "packaged" into an unlimited number of visual display formats commensurate with the most efficient and preferred eye tracking of that particular end-user.

In a similar manner, the visual analysis data can be used by the program 110 to create customized education/training modules to assist the end-user in the optimization of eye tracking. For example, an end-user is noted by the program 110 to repeatedly backtrack on certain types of data (e.g., numerical), while more efficiently processing the same data content displayed in an alternate content format (e.g., bar graphs). The visual data analysis can be used in two ways; the first would be to simply convert numerical data to alternate graphical representations (as applicable), while the second would be to create a tutorial on how to efficiently visualize and mentally process the numerical data. As the end-user navigates though the educational tutorial, the program 110 would provide feedback as to how the visual eye tracking analysis had demonstrated improvement and make recommendations for more efficient visualization. The color coded duration map created by the program 110 would provide an objective measure of feedback to the end-user to understand when, where, and for how long visual fixations take place and how to avoid them in the future.

This data can in turn be used to create user and context-specific automated visual display templates, in keeping with the individual end-user's eye tracking analysis. This would effectively create a motion picture which automatically presents visual data in the user-specific manner (or a preferred optimized manner, based upon visual data analysis) for the end-user to review. This would eliminate the need for the end-user to visually navigate through a complex visual display and instead present the data sequentially in a central filed of view. This has the added advantage or incorporating data points which are routinely being overlooked (i.e., non-visualized data points) by the end-user.

A timing device (i.e., pacer) can also be incorporated in the program 110 to assist the end-user in more efficient visualization, and reduce unnecessary fixations and dwell times. This can be created using several different options, one of which could consist of a signal (auditory, visual) which is presented to the end-user once a pre-defined time threshold has been reached. This threshold could be tied by the program 110 to individual dwell times (i.e., a single point of visualization), or collective visualization times of a collective data display.

While these visual display options and analytical feedback can be used to facilitate improved visual efficiency and data assimilation, they can also be applied to commercial purposes for the data (i.e., content) provider. An Internet advertiser and/or content provider could gain important data as to how visual data is being reviewed and better understand how visual data display can be optimized. Something as simple as a color coded visualization map which shows visualization times, could be pooled by the program 110 over large numbers of viewers to show how modification of a single visual display variable can impact how long end-users are viewing this data. The same principles of visual customization can be applied by the program 110 to maximize visualization among disparate end-users, in keeping with their individual eye tracking profiles.

Advertising payments could literally be tied to visual analysis, the longer and more frequent visualization occurs, the higher the payment to the content provider. Since visual display is ubiquitous in every life, all occupations and computer-based tasks would in some way be impacted.

Thus, it should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A method of utilizing an eye movement detection apparatus in a medical application, the medical application being a radiological application which obtains medical images by at least one of a magnetic resonance imaging (MRI) device, a computerized tomography (CT) imaging device, or an X-ray device, wherein during review and interpretation by a user of the medical images obtained during the radiological application, the user follows a pre-determined set of visual and cognitive steps, the method comprising:

measuring eye movements, including how an eye moves from one location to another, of the user using the eye movement detection apparatus, the eye movement detection apparatus having an optical recording system with a sensing device, said optical recording system being mounted on a user's headband and emitting infrared light which is reflected into a charge-coupled camera disposed next to said sensing device, and recording said eye movements;

providing a computer system which is connected to the eye movement detection apparatus;

receiving inputs from the user via said computer system, said inputs which are used by a processor of said computer system, to calibrate the eye movement detection apparatus to said user;

performing said predetermined set of visual and cognitive steps using the eye movement detection apparatus on a plurality of said medical images presented to said user on a display of said computer system, and storing information from said steps into a database to establish a baseline for said user;

determining a visual profile of a workflow of the user using an analysis of said stored information from said predetermined set of visual and cognitive steps, using said processor;

creating, using said processor, an automated visual display protocol of said workflow of said user, which is user specific, is stored in said database, and is provided on said display, such that said user can review said medical images using said automated visual display protocol;

storing in said database, eye-tracking commands inputted into said computer system from the eye movement detection apparatus, for individual user navigation and computer interactions;

storing context-specific eye-tracking commands from said user with respect to the medical application, which are inputted from the eye movement detection apparatus, into said database of said computer system;

performing the medical application on said medical images on said display of said computer system, using said eye-tracking commands; and storing eye-tracking data and results of an analysis performed by said processor, of data from performance of the medical application on said medical images, in said database.

2. The method according to claim 1, wherein said inputs from said user include individual preferences for data presentation by said computer system, and further comprising:

receiving input from training of said eye movements of said user with the eye movement detection apparatus, and storing said user input and said eye movements input in a database of said computer system;

wherein said inputs from said user and said eye movements training are part of a training program on the eye movement detection apparatus.

3. The method according to claim 1, wherein said eye-tracking commands include at least one of object selection, object movement, text scrolling, image scrolling, menu commands, or editing functions.

4. A non-transitory computer-readable medium whose contents cause a computer system to execute instructions of a program, the computer system being connected to an eye movement detection apparatus in a medical application, the medical application being a radiological application which obtains medical images by at least one of a magnetic resonance imaging (MRI) device, a computerized tomography (CT) imaging device, or an X-ray device, wherein during review and interpretation by a user of the medical images obtained during the radiological application, the user follows a predetermined set of visual and cognitive steps, the program comprising the steps of:

measuring eye movements, including how an eye moves from one location to another, of the user using the eye movement detection apparatus, the eye movement detection apparatus having an optical recording system with a sensing device, said optical recording system being mounted on a user's headband and emitting infrared light which is reflected into a charge-coupled camera disposed next to said sensing device, and recording said eye movements;

receiving inputs from the user via said computer system, said inputs which are used by a processor of said computer system, to calibrate the eye movement detection apparatus to said user;

performing said predetermined set of visual and cognitive steps using the eye movement detection apparatus on a plurality of said medical images presented to said user on a display of said computer system, and storing information from said steps into a database to establish a baseline for said user;

determining a visual profile of a workflow of the user using an analysis of said stored information from said predetermined set of visual and cognitive steps, using a processor of said computer system;

creating, using said processor, an automated visual display protocol of said workflow of said user, which is user specific, is stored in said database, and is provided on said display, such that said user can review said medical images using said automated visual display protocol;

storing in said database, eye-tracking commands inputted into said computer system from the eye movement detection apparatus, for individual user navigation and computer interactions;

storing context-specific eye-tracking commands from said user with respect to the medical application, which are inputted from the eye movement detection apparatus, into said database of said computer system;

performing the medical application on said medical images on said display of said computer system, using said eye-tracking commands; and storing eye-tracking data and results of an analysis performed by said processor, of data from performance of the medical application on said medical images, in said database.

5. A computer system which utilizes an eye movement detection apparatus in a medical application, the medical application being a radiological application which obtains medical images by at least one of a magnetic resonance imaging (MRI) device, a computerized tomography (CT) imaging device, or an X-ray device, wherein during review and interpretation by a user of the medical images obtained during the radiological application, the user follows a predetermined set of visual and cognitive steps, the computer system being connected to the eye movement detection apparatus, the computer system comprising:

at least one memory containing at least one program comprising the steps of:

measuring eye movements, including how an eye moves from one location to another, of the user using the eye movement detection apparatus, the eye movement detection apparatus having an optical recording system with a sensing device, said optical recording system being mounted on a user's headband and emitting infrared light which is reflected into a charge-coupled camera disposed next to said sensing device, and recording said eye movements;

receiving inputs from the user via said computer system, said inputs which are used by a processor of said computer system, to calibrate the eye movement detection apparatus to said user;

performing said predetermined set of visual and cognitive steps using the eye movement detection apparatus on a plurality of said medical images presented to said user on a display of said computer system, and storing information from said steps into a database to establish a baseline for said user;

determining a visual profile of a workflow of the user using an analysis of said stored information from said predetermined set of visual and cognitive steps, using at least one processor of said computer system;

creating, using said at least one processor, an automated visual display protocol of said workflow of said user, which is user specific, is stored in said database, and is provided on said display, such that said user can review said medical images using said automated visual display protocol;

storing in said database, eye-tracking commands inputted into said computer system from the eye movement detection apparatus, for individual user navigation and computer interactions;

storing context-specific eye-tracking commands from said user with respect to the medical application, which are inputted from the eye movement detection apparatus, into said database of said computer system;

performing the medical application on said medical images on said display of said computer system, using said eye-tracking commands;

storing eye-tracking data and results of an analysis performed by said at least one processor, of data from performance of the medical application on said medical images, in said database; and said at least one processor for executing the program.

6. A method of utilizing an eye movement detection apparatus in a medical application, the medical application being a radiological application which obtains medical images by at least one of a magnetic resonance imaging (MRI) device, a computerized tomography (CT) imaging device, or an X-ray device, wherein during review and interpretation by a user of the medical images obtained during the radiological application, the user follows a predetermined set of visual and cognitive steps, the method comprising:

measuring eye movements, including how an eye moves from one location to another, of the user using the eye movement detection apparatus, the eye movement detection apparatus having an optical recording system with a sensing device, said optical recording system being mounted on a user's headband and emitting infrared light which is reflected into a charge-coupled camera disposed next to said sensing device;

providing a computer system which is connected to the eye movement detection apparatus, said computer system including a database and a processor;

recording said eye movements, as measured by the eye movement detection apparatus, in the database;

determining a visual profile of a workflow of the user based on the recorded eye movements and in accordance with said predetermined set of visual and cognitive steps, using said processor; and creating, using said processor, an automated visual display protocol of said workflow of said user, such that said user can review said medical images using said automated visual display protocol.

7. The method according to claim 6, further comprising: utilizing said processor to forward from said computer system, via electronic means, individual profiles of said eye-tracking commands to other users for at least one of protocol optimization, education, or training.

8. The method according to claim 7, wherein said automated visual display protocol results in creating an automated visual workflow templates based upon data analysis of the user and reference peer groups by said processor.

9. The method according to claim 6, wherein said eye-tracking commands include at least one of blink, blink rate, gaze direction, or length of gaze.

10. The method according to claim 7, further comprising:
performing an analysis of said database, using said processor, for determining best practice guidelines based on clinical outcome measures.

11. The method according to claim 6, further comprising:
integrating said input from the eye movement detection apparatus with input from said computer system by correlating eye-tracking patterns of the user with fatigue and stress measurements.

12. The method according to claim 11, wherein the eye movement detection apparatus becomes sensitized to changes in a user's physical and emotional state and said processor automatically adjusts internal sensitivity settings of the eye movement detection apparatus to said changes.

13. The method according to claim 11, further comprising:
prompting the user using said processor, via electronic means, when changes in a user's physical and emotional state exceed a predetermined threshold.

14. The method according to claim 11, further comprising:
shutting down computer operations or mandating a rest period by the user, using said processor, until changes in the user's physical and emotional state return below a predetermined threshold.

15. The method according to claim 11, further comprising:
initiating a sequence of training/feedback steps using said processor, due to changes in a user's physical and emotional state as analyzed from said input from the eye movement detection apparatus and computer system; and
re-adjusting internal visual recognition parameters using said processor, due to completion of said sequence.

16. The method according to claim 6, wherein the medical application is performed using non-command based user interactions.

17. The method according to claim 8, further comprising:
performing an analysis of eye-tracking data, using said processor, including providing automated data extraction analysis on eye fixations and saccades by one of eye positioning or eye velocity.

18. The method according to claim 17, further comprising:
applying, using said processor, selective resolution and decompression algorithms, and specialized image processing of said medical images obtained during the radiological application.

19. The method according to claim 18, further comprising:
modifying and refining individual user's automated visual display protocol using said processor; and
processing automated visual workflow templates, using said processor, in accordance with the user's modified automated visual display protocol and in context with the medical application.

20. The method according to claim 6, wherein eye-tracking metrics recorded by said eye movement detection apparatus include gaze rate; gaze direction; gaze percentage; number of fixations; scan path directionality; number of instances of backtracking; frequency of long duration dwells over areas of interest; saccade length; and fixation/saccade time ratio.

21. The method according to claim 6, further comprising:
performing feedback operations using said processor, with the user, to assess an efficiency of the user during the medical application.

22. The method according to claim 21, wherein indicators of inefficiency include backtracking over a same visual area, or fixation over a visual area.

23. The method according to claim 21, further comprising:
obtaining a baseline measure of visual acuity and fatigue of the user using data from the eye movement detection apparatus and input from said computer system.

24. The method according to claim 20, further comprising:
recording visual metrics in numerical and graphical formats in said database of said computer system.

25. The method according to claim 24, further comprising:
creating visual maps, using said processor, which graphically show each of said eye-tracking commands in chronological order, with time-stamping of same.

26. The method according to claim 8, wherein a playback function cycles through the automated visual workflow template.

27. The method according to claim 17, further comprising:
providing an alert to users by electronic means, when deficiencies in said eye-tracking analysis is found using said processor.

28. The method according to claim 22, wherein a timing device forwards alerts by electronic means, to users when fixations are noted using said processor.

* * * * *